United States Patent [19]
Persing

[11] Patent Number: 6,087,097
[45] Date of Patent: *Jul. 11, 2000

[54] **PCR DETECTION OF *BORRELIA BURGDORFERI***

[75] Inventor: David H. Persing, Rochester, Minn.

[73] Assignee: Mayo Foundation for Medical Education and Research, Rochester, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/642,807

[22] Filed: May 3, 1996

Related U.S. Application Data

[63] Continuation of application No. 08/241,496, May 12, 1994, abandoned.

[51] Int. Cl.$^7$ .............................. C12Q 1/68; C12P 19/34; C07H 21/02; C07H 21/04
[52] U.S. Cl. ........................... 435/6; 435/91.1; 435/91.2; 536/24.3; 536/24.31; 536/24.32; 536/24.33
[58] Field of Search ........................... 435/6, 91.1, 91.2; 536/24.3, 24.31, 24.32, 24.33

[56] References Cited

U.S. PATENT DOCUMENTS

| | | | |
|---|---|---|---|
| 5,279,938 | 1/1994 | Rosa ............................................. | 435/6 |
| 5,530,103 | 6/1996 | Livey et al. ............................. | 530/416 |
| 5,582,990 | 12/1996 | Bergstrom et al. ......................... | 435/6 |

FOREIGN PATENT DOCUMENTS

| | | |
|---|---|---|
| 2001328 | 4/1991 | Canada . |
| 93/08306 | of 1993 | WIPO . |

OTHER PUBLICATIONS

Fellinger et al, Sequence of the complete osp operon encoding two major outer membrane proteins of a european *Borrelia burgdorferi* isolate (B29), Gene 120:127–128, 1992.
Coleman et al, Variations in the ospB gene of *Borrelia burgdorferi* result in differences in monoclonal antibody reactivity and in production of escape variants, Infection and Immunity 62(1):303–307, Jan. 1994.
Barbour, A.G., "Lyme Disease", *Infectious Diseases,* 5th ed., P.D. Hoeprich et al., eds., JB Lippincott Co., Philadelphia, PA, 1327–1332, (1994).
Coonrod, J.D., "Immunologic Diagnosis", *Infections Diseases,* 5th ed., P.D. Hoeprich et al., eds., JB Lippincott Company, Philadelphia, 187–194, (1994).
Norton–Hughes, C.A., et al., "Protective Immunity is Induced by a *Borrelia burgdorferi* Mutant that Lacks OspA and OspB", *Infection and Immunity,* vol. 61, 12, 5115–5122, (1993).
Sadziene, A., et al., "Antibody–Resistant Mutants of *Borrelia burgdorferi*: In Vitro Selection and Characterization", *J. of Exp. Med.,* 176, 799–809, (1992).

Sadziene, A., et al., "The Cryptic ospC Gene of *Borrelia burgdorferi* B31 is located on a circular plasmid", *Infection and Immunity,* 61, 5, 2192–2195, (1993).
Rys, "PCR detection of *Borrelia burgdorferi*" in Diagnostic Clinical Biology, D.H. Persing Ed., 1993, Am. Soc. Micro., Washington, D.C., p. 203–210.
Nielsen et al., "Detection of *Borrelia burgdorferi* DNA by the polymerase chain reaction", 1990, Mol. Cell. Probes 4:73–79.
Jonsson et al, "Heterogeneity of outer membrane proteins in *Borrelia burgdorferi*: Comparison of Osp operons of three isolates of different geographic origins", 1992, Infect. Immun. 60:1845–1853.
Persing et al, "Multitarget detection of *B. burgdorferi* associated DNA sequences in synovial fluid of patients with arthritis", 1990, Arthritis Rheum. 33:S36.
Cimino et al, "Post–PCR sterilization: a method to control carryover contamination for the polymerase chain reaction", 1990, Nuc. Acids Res. 19:99–107.
Fikrig et al, "Evasion of protective immunity by *Borrelia burgdorferi* by truncation of outer surface protein B", May 1993, PNAS 90:4092–4096.
Guy et al, "Detection of *Borrelia burgdorferi* in patients with Lyme disease by the polymerase chain reaction", 1991, J. Clin. Pathol. 44:610–611.
Williams et al, "Molecular diagnosisof *Borrelia burgdorferi* Infection (Lyme disease)", 1992, DNA and Cell Biology 11:207–213.
Picken, "Polymerase chain reaction primers and probes derived from flagellin gene sequences for specific detection of the agents of lyme disease and North American relapsing fever", 1992, J. Clin. Micro. 30:99–114.
Wallich et al, "Evaluation of genetic divergence among*Borrelia burgdorferi* isolates by use of OspA, fla, HSP60 and HSP70 gene probes", 1992, Infect. Immun. 60:4856–4866.
Malloy et al, "Detection of *Borrelia burgdorferi* using the polymerase chain reaction", 1990, J. Clin. Micro. 28:1089–1093.
Zumstein et al, "Genetic polymorphism of the gene encoding the outer surface protein A (Osp A) of *Borrelia burgdorferi*", 1992, Med. Microbiol. Immunol. 181:57–70.

(List continued on next page.)

*Primary Examiner*—Jeffrey Fredman
*Attorney, Agent, or Firm*—Schwegman, Lundberg, Woessner & Kluth P.A.

[57] ABSTRACT

A method for detecting in a biological sample the presence of Lyme-disease causing spirochetes using the polymerase chain reaction (PCR). This method includes the steps of: isolating DNA from the biological sample; amplifying the isolated DNA under hybridizing conditions with a primer pair that targets portions of extrachromosomal linear plasmid gene encoding outer surface protein A (OspA) or outer surface protein B (OspB) of the Lyme-disease causing spirochetes, probing the amplified DNA under hybridizing conditions with a labeled gene probe; and detecting the labeled gene probe that hybridized to the amplified DNA of the Lyme-disease causing spirochetes.

13 Claims, 22 Drawing Sheets

OTHER PUBLICATIONS

Schwartz et al, "Diagnosis of early lyme disease by polymerase chain reaction amplification and culture of skin biopsies from *Erythema Migrans* lesions", 1992, J. Clin. Micro. 30:3082–3088.

Liebling et al, "The polymerase chain reaction for the detection of *Borrelia burgdorferi* in human body fluids", 1993 May, Arthritis Rheum. 36:665–675.

Marconi et al, "Variability of osp genes and gene products among species of Lyme disease spirochetes", 1993, Inf. Immun. 61:2611–2617.

Sommer et al, (1989), "Minimal homology requirements for PCR primers", Nucleic Acids Research 17(16):6749.

Sogin, (1990), "Amplification of ribosomal RNA genes for molecular evolution studies", In PCR Protocols: A Guide to Methods and Applications, Innis et al Eds, Academic Press, San Diego, CA, pp 307–314.

S.W. Barthold, "A Rat Model of Lyme Disease," Abstract of National Institutes of Health Grant No. AI26815 (Funding Year: 1994). Abstract obtained from the Dialog database Federal Research in Progress.

S. Bergstrom, "*Borrelia burgdorferi* OspA and OspB Genes for Major Outer Membrane Proteins," GenBank Accession No. X14407 (Aug. 27, 1993).

S. Bergstrom, "Molecular Analysis of Linear Plasmid–Encoded Major Surface Proteins, OspA and OspB, of the Lyme Disease Spirochaete *Borrelia burgdorferi*,", Mol. Microbiol., 3, 479–486 (1989).

H. Eiffert, "*B. burgdorferi* OspA Gene for OspA Outer Surface Protein," GenBank Accession Nos. X60300 and S99475 (Dec. 7, 1992).

E. Fikrig et al., "Outer Surface Protein A [*Borrelia burgdorferi*, strain 35015, Genomic, 819 nt]," GenBank Accession No. S88693 (Jul. 10, 1992).

E. Fikrig et al., "*B. burgdorferei* Outer Surface Protein A (ospA) Gene, complete cds," GenBank Accession Nos. M57248 and M38375 (Nov. 14, 1991).

C.F. Garon, "Structural Characterization of Microbial Genes and Nucleic Acid Molecules," Abstract of National Institutes of Health Grant No. AI00554 (Funding Year: 1994). Abstract obtained from the Dialog database Federal Research in Progress.

E. Godfroid et al., "*B. burgdorferi* (G25) OspA Gene for Outer Surface Protein A," GenBank Accession No. Z29086 (Dec. 20, 1993).

E. Godfroid et al., "*B. burgdorferi* (VS461) OspA Gene for Outer Surface Protein A," GenBank Accession No. Z29087 (Dec. 20, 1993).

J.L. Goodman et al., "Molecular Detection of Persistent *Borrelia burgdorferi* in Urine of Patients with Active Lyme Disease," Infect. Immun., 59, 269–278 (1991).

D.U. Leong et al., "PCR Detection of Bacteria Found in Cerebrospinal Fluid," in *Diagnostic Molecular Microbiology: Principles and Applications;* D.H. Persing et al., Eds.; American Society for Microbiology: Washington, DC; pp. 300–308 (1993).

B.J. Luft, "*B. burgdorferi* OspA Gene," GenBank Accession No. X62624 (Jan. 12, 1994).

B.J. Luft, "*B. burgdorferi* OspA Gene for Outer Surface Protein A," GenBank Accession No. X63387 (Jan. 12, 1994).

S.E. Malawista et al., "Failure of Multitarget Detection of *Borrelia burgdorferi*–associated DNA Sequences in Synovial Fluids of Patients with Juvenile Rheumatoid Arthritis: a Cautionary Note," Arthritis Rheum., 35, 246–247 (Feb. 1992).

S. Malawista, "Probes for *Borrelia burgdorferi* DNA in Ticks, Mice and Men," Abstract of National Institutes of Health Grant No. AI30548 (Funding Year: 1994). Abstract obtained from the Dialog database Federal Research in Progress.

P.D. Mitchell et al., "Isolation of *Borrelia burgdorferi* From Skin Biopsy Specimens of Patients with *Erythema Migrans,*" Am. J. Clin. Pathol., 99, 104–107 (Jan. 1993).

J. J. Nocton et al., "Detection of *Borrelia Burgdorferi* DNA by Polymerase Chain Reaction in Synovial Fluid from Patients with Lyme Arthritis," N. Eng. J. Med., 330, 229–234 (Jan. 1994).

D.H. Persing, "Molecular Diagnosis and Monitoring of Lyme Disease," Abstract of National Institutes of Health Grant No. AR41497 (Funding Year: 1994). Abstract obtained from the Dialog database Federal Research in Progress.

D.H. Persing, "Multi–Locus Molecular Detection of *Borrelia Burgdorferi*," Abstract of National Institutes of Health Grant No. AI32403 (Funding Year: 1994). Abstract obtained from the Dialog database Federal Research in Progress.

D.H. Persing et al., "Target Imbalance: Disparity of *Borrelia burgdorferi* Genetic Material in Synovial Fluid from Lyme Arthritis Patients," J. Infect. Dis., 169, 668–672 (Apr. 1994).

D.H. Persing et al., "Detection of *Borrelia burgdorferi* DNA in Museum Specimens of *Ixodes dammini* Ticks," Science, 249, 1420–1423 (Sep. 1990).

D.H. Persing et al., "Detection of *Borrelia burgdorferi* Infection in *Ixodes dammini* Ticks with the Polymerase Chain Reaction," J. Clin. Microbiol., 28, 566–572 (Mar. 1990).

D.H. Persing et al., "Multi–Target Detection of *B. burgdorferi*–associated DNA Sequences in Synovial Fluids of Patients with Arthritis," Abstract No. 162, Arthritis Rheum., 33 (suppl) p. S36 (1990).

D.H. Persing, "Molecular Detection of *Borrelia burgdorferi*," in *Lyme Disease: Molecular and Immunologic Approaches;* S. Schutzer, ed.; Cold Spring Harbor Laboratory Press: Cold Spring Harbor, NY; 229–315 (1993).

D.H. Persing et al., "Detection of *Babesia microti* by Polymerase Chain Reaction," J. Clin. Microbiol., 30, 2097–2103 (Aug. 1992).

D.H. Persing et al., "Amplification Product Inactivation Methods," in *Diagnostic Molecular Microbiology: Principles and Applications;* D.H. Persing et al., Eds.,; American Society for Microbiology: Washington; 105–121 (1993).

D.H. Persing et al., "In Vitro Nucleic Acid Amplification Techniques," in *Diagnostic Molecular Microbiology: Principles and Applications;* D.H. Persing et al., Eds.; American Society for Microbiology: Washington; 51–87 (1993).

D.H. Persing et al., "Target Selection and Optimization of Amplification Reactions," in *Diagnostic Molecular Microbiology: Principles and Applications;* D.H. Persing et al., Eds.; American Society for Microbiology: Washington; 88–104 (1993).

R.N. Picken, "Lyme Disease Diagnosis by PCR/DNA Probe System," Abstract of National Institutes of Health Grant No. AR41517 (Funding Year: 1994). Abstract obtained from the Dialog database Federal Research in Progress.

P.A. Rosa et al., "A Specific and Sensitive Assay for the Lyme Disease Spirochete *Borrelia burgdorferi* Using the Polymerase Chain Reaction," *J. Infect. Dis.,* 160, 1018–1029 (Dec. 1989).

P.N. Rys, "PCR Detection of *Borrelia burgdorferi*," in *Diagnostic Molecular Microbiology: Principles and Applications;* D.H. Persing et al., Eds.; American Society for Microbiology: Washington; 203–210 (May 13, 1993).

P.N. Rys et al., "Preventing False Positives: Quantitative Evaluation of Three Protocols for Inactivation of Polymerase Chain Reactions Amplification Products," *J. Clin. Microbiol.,* 31, 2356–2360 (Sep. 1993).

T.G. Schwan, "Molecular Basis for Infection by *Borrelia Burgdorferi*," Abstract of National Institutes of Health Grant No. AI00492 (Funding Year: 1994). Abstract obtained from the Dialog database Federal Research in Progress.

I.S. Schwartz, "Nucleic Acid–Based Diagnostic Probes for Lyme Disease," Abstract of National Institutes of Health Grant No. AR41511 (Funding Year: 1994). Abstract obtained from the Dialog database Federal Research in Progress.

A.C. Steere, "Lyme Disease," *N. Eng. J. Med.,* 321, 586–596 (Aug. 1989).

F.C. Tenover et al., "Nucleic Acid Probes for Detection and Identification of Infectious Agents," in *Diagnostic Molecular Microbiology: Principles and Applications;* D.H. Persing et al., Eds., American Society for Microbiology: Washington; 3–25 (1993).

R. Wallich, "*B. burgdorferi* OspA Gene for Outer Surface Protein A," GenBank Accession Nos. X68059 and S46719 (Sep. 20, 1993).

R. Wallich, "*B. burgdorferi* OspA Gene for Outer Surface Protein A," GenBank Accession Nos. X66065 and S46718 (Jul. 25, 1993).

R. Wallich, "*B. burgdorferi* OspA Gene for Outer Surface Protein A," GenBank Accession No. X16467 (Jan. 2, 1990).

T.J. White et al., "The Polymerase Chain Reaction: Clinical Applications," *Adv. Clin. Chem.,* 29, 161–196 (1992).

T.J. White, "Amplification Product Detection Methods," in *Diagnostic Molecular Microbiology: Principles and Applications;* D.H. Persing et al., Eds.; American Society for Microbiology: Washington; 138–148 (1993).

W.V. Williams, et al., "Detection of *Borrellia burgdorfei* by DNA Amplification", Abstract No. 161, *Arthritis Rheum.,* 33, (suppl) p. S36 (1990).

W.V. Williams, et al., "Molecular Diagnosis of *Borrelia burgdorferi* Infection (Lyme Disease)," *DNA Cell Biol.,* 11, 207–213 (1992).

G. Zumstein et al., "OspA = Outer Surface Protein A [*Borrelia burgdorferi*, cerebrospinal fluid isolate PBi, Genomic, 839 nt]," GenBank Accession No. S48323 (Jan. 14, 1993).

G. Zumstein et al., "OspA = Outer Surface Protein A [*Borrelia burgdorferi*, skin isolate Pko, Genomic 882 nt]," GenBank Accession No. S48322 (Jan. 8, 1993).

```
Base number (B31)     1                                                    50
Strain N40  {M57248}* ..........  ..........  ..........  ..........  ..........
Strain Zs7  {X16467}  ..........  ..........  ..........  ..........  ..........
Strain B31  {X14407}* aagctt  tt  agaacc aac  t  aa  ta  aa  ..........  ..........
Strain 25015{S88693}* ..........  ..........  ..........  ..........  ..........
       Strain Dn127*  ..........  ..........  ..........  ..........  ..........
Strain Pko  {S48322}  ..........  ..........  ..........  ..........  ..........
Strain Vs461{Z29087}  ..........  ..........  ..........  ..........  ..........
Strain Pgau {X62387}  ..........  ..........  ..........  ..........  ..........
Strain G25  {Z29086}  ..........  ..........  aa gtttat ttt g tc at tc ta tttag  ..........
Strain Goe2 {X60300}  ..........  ..........  ..........  ..........  atta c
Strain K48  {X62624}  ..........  ..........  ..........  ..........  ..........
Strain Zq1  {X66065}  ..........  ..........  ..........  ..........  ..........
Strain Pbi  {S48323}  ..........  ..........  ..........  ..........  ..........
Strain 19857{X68059}  ..........  ..........  ..........  ..........  ..........

Consensus             ------AA--  ------A---  -T--T--A--  CCAAACTTAA  TTGAAGTTAT
```

\* North American strains; others are European isolates.

FIG. 1A

```
Base number (B31)     51                                                                              100
Strain N40  {M57248}  .................................................
Strain Zs7  {X16467}  .................................................                      at        tat
Strain B31  {X14407}  .................................................                      at        tat
Strain 25015 {S88693} .................................................
Strain Dn127          .................................................
Strain Pko  {S48322}  .................................................                   ta           ata
Strain Vs461 {Z29087} .................................................
Strain Pgau {X62387}  .................................................
Strain G25  {Z29086}  ......t at.......................t   caa        tc ta         g ta    tg tga c
Strain Goe2 {X60300}  .................................................                   ta           ata
Strain K48  {X62624}  .................................................
Strain Zq1  {X66065}  .................................................
Strain Pbi  {S48323}  .................................................
Strain 19857 {X68059} .................................................

Consensus  TATCATTTTA TTTTTTTTCA ATTTTCTATT TGTTATTTGT TA--CT---A
```

FIG. 1B

| Base number (B31) | 101 | | | | | | | 150 |
|---|---|---|---|---|---|---|---|---|
| Strain N40 {M57248} | . . . . . . . . . . | . . . . . . . . . . | . . . . . . . . . . | . . . . . . . . . . | . . . . . . . . . . | . . . . . . . . . . | . . . . . . . . . . | . . . . . . . . . . |
| Strain Zs7 {X16467} | a | a | c tgta ta | g t | t | atat | | |
| Strain B31 {X14407} | a | a | c tgta ta | g t | t | atat | | |
| Strain 25015 {S88693} | . . . . . . . . . . | . . . . . . . . . . | . . . . . . . . . . | . . . . . . . . . . | . . . . . . . . . . | . . . . . . . . . . | . . . . . . . . . . | . . . . . . . . . . |
| Strain Dn127 | | | | | | | | |
| Strain Pko {S48322} | t | c g | t aagt at | t a | a | tata | | |
| Strain Vs461 {Z29087} | | | | | | | | |
| Strain Pgau {X62387} | | | | | | | | |
| Strain G25 {Z29086} | | | | | | | | |
| Strain Goe2 {X60300} | t | t g | t aagt at | t a | a | tata | | |
| Strain K48 {X62624} | | | | | | | | |
| Strain Zq1 {X66065} | | | | | | | | |
| Strain Pbi {S48323} | | | | | | | g cc c | |
| Strain 19857 {X68059} | | | | | | | | |
| Consensus | -TATAATT-T | A-T----T-- | A-T-ATAT-A | ---- | AAAAGG | AGAATATATT | | |

FIG. 1C

```
Base number (B31)          151                                               200
Strain N40  {M57248}       ...........................................
Strain Zs7  {X16467}       ...........................................
Strain B31  {X14407}       ...........................................
Strain 25015 {S88693}      ...........................................
Strain Dn127               .....................................t.....
Strain Pko  {S48322}       ...........................................
Strain Vs461 {Z29087}      ...........................................
Strain Pgau {X62387}       ...........................................
Strain G25  {Z29086}       ...........................................
Strain Goe2 {X60300}       ...........................................
Strain K48  {X62624}       ...........................................
Strain Zq1  {X66065}       ...........................................
Strain Pbi  {S48323}       ...........................................
Strain 19857 {X68059}      ...........................................

OSPA149
Consensus   ATGAAAAAAT ATTTATTGGG AATAGGTCTA ATATTAGCCT TAATAGCATG
                                    Region 1
```

| Base number (B31) | 201 | | | | | | | | | | | | | | | | | | | | | | | | | | | | | | | | | | | | | | | | | | | | | | | | 250 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Strain N40 {M57248} | | | | | | | | | | | | | | | | | | | | | | | | | | | | | | | | | | | | | | | | | | | | | | | | | | |
| Strain Zs7 {X16467} | | | | | | | | | | | c | g | | | | | | | | | | | | | | | | | | | | | | | | | | | | | | | | | | | | | | |
| Strain B31 {X14407} | | | | | | | | | | | c | g | | | | | | | | | | | | | | | | | | | | | | | | | | | | | | | | | | | | | | |
| Strain 25015 {S88693} | | | | | | | | | | | c | g | | | | | | | | | | | | | | | | | | | | | | | | | | | | | | | | | | | | | | |
| Strain Dn127 | | | | | | | | | | | | g | | | | | | | | | | | | | | | | | | | | | | | | | | | | | | | | | | | | | | |
| Strain Pko {S48322} | c | | | | | | | | | | | | | | | | | | | | | | | | | | | | | | | | | | | | | | | | | | | | | | | | | |
| Strain Vs461 {Z29087} | c | | | | | | | | | | | | | | | | | | | | | | | | | | | | | | | | | | | | | | | | | | | | | | | | | |
| Strain Pgau {X62387} | c | | | | | | | | | | | | | | | | | | | | | | | | | | | | | | | | | | | | | | | | | | | | | | | | | |
| Strain G25 {Z29086} | | | | | | | | | | | | | | | | | | | | | | | | | | | | | | c | | | | | | | t | | | | | | | | | | | | | |
| Strain Goe2 {X60300} | | | | | | | | | | | | | | | | | | | | | | | | | | | | | | c | | | | | | | t | | | | | | | | | | | | | |
| Strain K48 {X62624} | | | | | | | | | | | | | | | | | | | | | | | | | | | | | | | | | | | | | | t | | | | | | | | | | | | |
| Strain Zq1 {X66065} | | | | | | | | | | | | | | | | | | | | | | | | | | | | | | c | | | | | | | t | | | | | | | | | | | | | |
| Strain Pbi {S48323} | | | | | | | | | | | | | | | | | | | | | | | | | c | g | | | | | | | | | | | | | | | | | | | | | | | | |
| Strain 19857 {X68059} | | | | | | | | | | | c | g | | | | | | | | | | | | | | | | | | | | | | | | | | | | | | | | | | | | | | g |

Consensus  TAAGCAAAAT GTTAGCAGCC TTGATGAAAA AAACAGCGTT TCAGTAGATT

FIG. 1F

```
Base number (B31)             251                                                    300
Strain N40   {M57248}                              c                                  c
Strain Zs7   {X16467}                              c                           a      c
Strain B31   {X14407}                                                          a      c
Strain 25015 {S88693}                              c                           a      c
Strain Dn127                  ..................................................
Strain Pko   {S48322}              g
Strain Vs461 {Z29087}              g
Strain Pgau  {X62387}              g
Strain G25   {Z29086}       a      g   c
Strain Goe2  {X60300}       a      g   c
Strain K48   {X62624}       a      g   c  aa
Strain Zq1   {X66065}       a      g                                  c            t
Strain Pbi   {S48323}       a                                         c            t
Strain 19857 {X68059}       a      g   c                                      a      c Consensus   TGCCTGGTGA AATGAAAGTT CTTGTAAGTA AAGAAAAAGA CAAAGACGGT
```

| Base number (B31) | 301 | | | 350 |
|---|---|---|---|---|
| Strain N40 {M57248} | | ga | tt | |
| Strain Zs7 {X16467} | | ga | tt | |
| Strain B31 {X14407} | | ga | tt | |
| Strain 25015 {S88693} | | | t | a |
| Strain Dn127 | | | | |
| Strain Pko {S48322} | a | | | a |
| Strain Vs461 {Z29087} | a | | | a a |
| Strain Pgau {X62387} | a | | | a a |
| Strain G25 {Z29086} | a | g | | |
| Strain Goe2 {X60300} | a | g | | |
| Strain K48 {X62624} | a | g | | |
| Strain Zq1 {X66065} | a | g | | |
| Strain Pbi {S48323} | | t | | |
| Strain 19857 {X68059} | ga | | | |
| | g | c g a t | | |

Consensus AAGTACAGTC TAAAGGCAAC AGTAGACAAG CTTGAGCTTA AGGAACTTC

OSPA319

| Base number (B31) | 351 | ... | 400 |
|---|---|---|---|
| Strain N40 {M57248} | | | |
| Strain Zs7 {X16467} | | a g | c |
| Strain B31 {X14407} | | a g | c |
| Strain 25015 {S88693} | | a gg g | c |
| Strain Dn127 | | a ga | c |
| Strain Pko {S48322} | g | gg g | ac a |
| Strain Vs461 {Z29087} | g | g g | ac a |
| Strain Pgau {X62387} | g | g g | ac a |
| Strain G25 {Z29086} | c | ac | a a |
| Strain Goe2 {X60300} | c | ac | a a |
| Strain K48 {X62624} | c | ac | a a |
| Strain Zq1 {X66065} | c | ac | a a |
| Strain Pbi {S48323} | g | a | a t |
| Strain 19857 {X68059} | c | a | c t |

Consensus: TGATAAAAAC AATGGTTCTG GA-TACTTGA AGGTGTAAAA GCTGACAAAA

FIG. 1I

```
Base number (B31)           401                                              450
Consensus            GTAAAGTAAA ATTAACAATT GCTGACGATC TAAGTAAAAC CACATTTGAA
Strain N40  {M57248}
Strain Zs7  {X16467}                  c                t           g c
Strain B31  {X14407}                  c                t           g c
Strain 25015 {S88693} c               c                t           g c
Strain Dn127          c                            g   t             c c c
Strain Pko  {S48322}
Strain Vs461 {Z29087}                                          t c   g c    c c
Strain Pgau {X62387}                                                        c c
Strain G25  {Z29086}                                           t c   g c   t a
Strain Goe2 {X60300}                                           t c     c   t a
Strain K48  {X62624}                                           t c         t a
Strain Zq1  {X66065}                                           g
Strain Pbi  {S48323}   c                       g       t       a
Strain 19857 {X68059}                                  c             c       c
```

```
Base number  (B31)         451                                                500
Strain N40   {M57248}                              c                          c
Strain Zs7   {X16467}                              c                          c
Strain B31   {X14407}                              c                          c
Strain 25015 {S88693}                 c a                        g
Strain Dn127                          c a
Strain Pko   {S48322}       c                                  g g       a g    c
Strain Vs461 {Z29087}       c                                  g g       a c
Strain Pgau  {X62387}       c a                                g g       g    cct
Strain G25   {Z29086}       a                                                g cct
Strain Goe2  {X60300}       a             c                                  g cct
Strain K48   {X62624}       a                                                g cct
Strain Zq1   {X66065}       a                                                a
Strain Pbi   {S48323}       a          . . .         t        g         g      c
Strain 19857 {X68059}
```

Consensus  GTTTTCAAAAG AAGATGGCAA AACATTAGTA TCAAAAAAAG TAACTTCTAA
                   OSPA459                  Region 3

FIG. 1J

```
Base number (B31)           501                                                           550
Strain N40  {M57248}                                                                 g
Strain Zs7  {X16467}                                                                 g
Strain B31  {X14407}                                                                 g
Strain 25015 {S88693}        t                                          .c     c
Strain Dn127
Strain Pko  {S48322}                 aa            t    g                      c   gt
Strain Vs461 {Z29087}                aa            t    tg              c g    c    g
Strain Pgau {X62387}                 aa            t    tg              c g         g
Strain G25  {Z29086}                               t    tg              c g         g
Strain Goe2 {X60300}                                                  c c           ac
Strain K48  {X62624}                                                  c c           ac
Strain Zq1  {X66065}                                                  c c           ac
Strain Pbi  {S48323}         t                 c                      c c           a
Strain 19857 {X68059}                      a   t                        c           g Consensus   AGACAAGTCA TCAACAGAAG AAAAATTCAA TGAAAAGGT GAATTATCTG
                                   Region 3
```

FIG. 1K

```
Base number (B31)      551                                              600
Strain N40   {M57248}       t         t                              t
Strain Zs7   {X16467}       t         t                              t
Strain B31   {X14407}       t         t                              t
Strain 25015 {S88693}       t        gg                              t
Strain Dn127                         gt                            g  g
Strain Pko   {S48322}  c    c   a    g         c                      g
Strain Vs461 {Z29087}  c    c   a    g         c   t   a              g
Strain Pgau {X62387}   c    c   a    g         c       a              a
Strain G25   {Z29086}               gt         t                      g
Strain Goe2  {X60300}               gt         t                      a
Strain K48   {X62624}               gt         t              c       a
Strain Zq1   {X66065}               gt         t              c       a
Strain Pbi   {S48323}               gt         t              c       a
Strain 19857 {X68059}               ct         c       g  ct          g
                                     g Consensus            AAAAAACAAT AACAAGAGCA AA-GGAACCA GACTTGAATA CACAGAAAT-
```

FIG. 1L

```
Base number (B31)        601                                             650
Strain N40  {M57248}                                          g  a  a gt
Strain Zs7  {X16467}                                       g ag  a  a gt
Strain B31  {X14407}                                       g  g  a  a gt
Strain 25015 {S88693}                       t              ac    a  a gt
Strain Dn127                                t              ac       a g
Strain Pko  {S48322}                  a...                             a
Strain Vs461 {Z29087}                 a...                             a
Strain Pgau {X62387}                  a...                           a g
Strain G25  {Z29086}
Strain Goe2 {X60300}
Strain K48  {X62624}
Strain Zq1  {X66065}
Strain Pbi  {S48323}                 a...
Strain 19857 {X68059}                                      g Consensus  c at  a  acaatg  t c      agt    a  acc  t   a  ggc  t
           AAAAGCGATG GAT--CCGG AAAAGCTAAA GAAGTTTAA AAGACTTTAC
```

```
Base number (B31)      651                                              700
Strain N40  {M57248}                    t   a
Strain Zs7  {X16467}                    t   a
Strain B31  {X14407}                        a
Strain 25015 {S88693}                       a
Strain Dn127            g                   a            g       tg   a
Strain Pko  {S48322}              aag   a a a      ...t  g       tg   a
Strain Vs461 {Z29087}             aag   a a a      ...t  gt      tg   a
Strain Pgau {X62387}              aag   a a a      ...t  gt      tg   a
Strain G25  {Z29086}                                  c   gt      tg   a   a
Strain Goe2 {X60300}                                  c               a   c
Strain K48  {X62624}                                  c               a   c
Strain Zq1  {X66065}                                  c               a   c
Strain Pbi  {S48323}                                  c               a   c
Strain 19857 {X68059}            aagttt a  ggaaatctc  ...ac  aagt     a   c Consensus               TCTTGAAGGA ACTCTAGCTG CTGACGGAAA AACAACATTG GAAGTTAAAG
```

FIG. 10

```
Base number (B31)        701                                                  750
Strain N40  {M57248}                    t    a                         g  tt
Strain Zs7  {X16467}                    t    a                         g  tt
Strain B31  {X14407}                    t    a                         g  tt
Strain 25015 {S88693}                   t         c
Strain Dn127
Strain Pko  {S48322}         c          t    c    g
Strain Vs461 {Z29087}        c          t    g a  g
Strain Pgau {X62387}         c          t    g a  g
Strain G25  {Z29086}            gt           g a               c          a
Strain Goe2 {X60300}         c  gt                        t    c          a
Strain K48  {X62624}         c  gt                        t    c          a
Strain Zq1  {X66065}         c  gt                        t    c          a
Strain Pbi  {S48323}         c  gt                        t              a
Strain 19857 {X68059}        c       c  aa  ac  gag a  g at  aa            a    c Consensus               AAGGAACTGT TACTTTAAGC AAGAACATTT CAAAATCTGG AGAAGTAACA
```

```
Base number (B31)       751                                      800
Strain N40   {M57248}    a           a           g g gct         c gc
Strain Zs7   {X16467}    a           a           g g gct         c gc
Strain B31   {X14407}    a           a           g g gct         c gc
Strain 25015 {S88693}    c                       g   a           g  a
Strain Dn127             c           ag          tg  g           a
Strain Pko   {S48322}    t     a                                 cgc
Strain Vs461 {Z29087}    t   t a                                 cgc
Strain Pgau {X62387}     t   t a                                 cgc
Strain G25   {Z29086}        g   t                               a
Strain Goe2  {X60300}        g   t                               a
Strain K48   {X62624}        g   t                               a
Strain Zq1   {X66065}            t                               a
Strain Pbi   {S48323}   ag    a     c at .......     g t       a cttc
Strain 19857 {X68059}   ct tt a Consensus  GTTGCACTTA ATGACACTGA CACTACTCAG GCTACTAAAA AAACTGGAA-
```

```
Base number (B31)            801                                          850
Strain N40   {M57248}         t       a       ggc                                  a                t
Strain Zs7   {X16467}         t       a       ggc                                  a                t
Strain B31   {X14407}         t       a       ggc                                  a                t
Strain 25015 {S88693}                         ggc                        c         a
Strain Dn127                          g       gg                                   a
Strain Pko   {S48322}                 g g     gg                         c         t
Strain Vs461 {Z29087}                                                              t   t
Strain Pgau  {X62387}                                                              t   t
Strain G25   {Z29086}                         g                                        t   c  g  t  c
Strain Goe2  {X60300}                         g                                            g  t     c
Strain K48   {X62624}                         g                                            g  t     c
Strain Zq1   {X66065}                         t                                            g  t     c
Strain Pbi   {S48323}                                                                      g
Strain 19857 {X68059}   c  c  aga     gt  ag                    c                                  c Consensus   ATGGGATTCA AAAACTTCCA CTTTAACAAT TAGTGTAAAC AGCAAAAAAA
```

FIG. 1R

```
Base number (B31)              851                                              900
Strain N40  {M57248}                                        a                c
Strain Zs7  {X16467}                   g           t        a                c
Strain B31  {X14407}                   g           t        a                c
Strain 25015 {S88693}                  gc a        t                        tc
Strain Dnl27
Strain Pko  {S48322}           c   c c a  g      t g c           t
Strain Vs461 {Z29087}          c   c c a  g      t g c           t
Strain Pgau {X62387}           c   c c a  g      t g c        a  t
Strain G25  {Z29086}                   a  a c         c
Strain Goe2 {X60300}           c       a  a c         c
Strain K48  {X62624}           c       a  a c         c
Strain Zq1  {X66065}           c       a    c                 a c
Strain Pbi  {S48323}                 a a
Strain 19857 {X68059}                                                           t t Consensus        CTAAAAACCT TGT-TTACA AAAGAAGACA CAATAACAGT ACAAAAATAC
                          g t a g cct  c a c gt   t
```

FIG. 1S

```
Base number (B31)        901                                              950
Strain N40   {M57248}         aat                a        gt              c  a
Strain Zs7   {X16467}         aat                a   g    gt    t         c  a
Strain B31   {X14407}         aat                a   g    gt    t         c  a
Strain 25015 {S88693}              a             c        g     t         a  a
Strain Dn127                                     c        g               a
Strain Pko   {S48322}              c                                      a
Strain Vs461 {Z29087}              c                                      a
Strain Pgau  {X62387}              c                            g         c
Strain G25   {Z29086}              t        c             a               c
Strain Goe2  {X60300}              t        c             a               c
Strain K48   {X62624}                        c            a               c
Strain Zq1   {X66065}                        c            a               a
Strain Pbi   {S48323}                        c            ac               a
Strain 19857 {X68059}   t            t   ac  t            at     ct        a  a Consensus              GACTCAGCAG GCACCAATTT AGAAGGCACA GCAGTCGAAA TTA-AACACT
```

FIG. 1T

```
Base number (B31)           951                                              1000
Strain N40  {M57248}                  a  a
Strain Zs7  {X16467}                  a  a
Strain B31  {X14407}                  a                       g tt        taa
Strain 25015 {S88693}
Strain Dn127
Strain Pko  {S48322}        g
Strain Vs461 {Z29087}       g
Strain Pgau {X62387}
Strain G25  {Z29086}     a a           g
Strain Goe2 {X60300}     a a           g                                a ca  att
Strain K48  {X62624}     a a
Strain Zq1  {X66065}     a a
Strain Pbi  {S48323}                              a ga t c
Strain 19857 {X68059}    c                g Consensus                  TGATGAACTT AAAAACGCTT TAAAATAAGG AGAATTTATG A-A--AT---
```

| Base number (B31) | 1001 | | | | 1050 |
|---|---|---|---|---|---|
| Strain N40 {M57248} | . . . . . . . . . . | . . . . . . . . . . | . . . . . . . . . . | . . . . . . . . . . | . . . . . . . . . . |
| Strain Zs7 {X16467} | . . . . . . . . . . | . . . . . . . . . . | . . . . . . . . . . | . . . . . . . . . . | . . . . . . . . . . |
| Strain B31 {X14407} | . . gga . . . . . . | . . gc ttt gcgtt | . . . . ttt gcgtt | gcttta t g gatg gc ca | . . . . ggtgct |
| Strain 25015 {S88693} | . . . . . . . . . . | . . . . . . . . . . | . . . . . . . . . . | . . . . . . . . . . | . . . . . . . . . . |
| Strain Dn127 | . . . . . . . . . . | . . . . . . . . . . | . . . . . . . . . . | . . . . . . . . . . | . . . . . . . . . . |
| Strain Pko {S48322} | . . . . . . . . . . | . . . . . . . . . . | . . . . . . . . . . | . . . . . . . . . . | . . . . . . . . . . |
| Strain Vs461 {Z29087} | . . . . . . . . . . | . . . . . . . . . . | . . . . . . . . . . | . . . . . . . . . . | . . . . . . . . . . |
| Strain Pgau {X62387} | . . . . . . . . . . | . . . . . . . . . . | . . . . . . . . . . | . . . . . . . . . . | . . . . . . . . . . |
| Strain G25 {Z29086} | . . . . . . . . . . | . . . . . . . . . . | . . . . . . . . . . | . . . . . . . . . . | . . . . . . . . . . |
| Strain Goe2 {X60300} | . . ccg ta aac ctagc | . . . . . . . . . . | aaacag a a atat tg ac | . . . . atcttc | . . . . atcttc |
| Strain K48 {X62624} | . . . . . . . . . . | . . . . . . . . . . | . . . . . . . . . . | . . . . . . . . . . | . . . . . . . . . . |
| Strain Zq1 {X66065} | . . . . . . . . . . | . . . . . . . . . . | . . . . . . . . . . | . . . . . . . . . . | . . . . . . . . . . |
| Strain Pbi {S48323} | . . . . . . . . . . | . . . . . . . . . . | . . . . . . . . . . | . . . . . . . . . . | . . . . . . . . . . |
| Strain 19857 {X68059} | . . . . . . . . . . | . . . . . . . . . . | . . . . . . . . . . | . . . . . . . . . . | . . . . . . . . . . |
| Consensus | TA---TTT-- ---A----A | ---A----A | -----A-A- | ---T--A-- | AAAA---- |

FIG. 1U

| Base number (B31) | 1051 | | | | | | 1100 |
|---|---|---|---|---|---|---|---|
| Strain N40 {M57248} | . . . . . . . . . . | . . . . . . . . . . | . . . . . . . . . . | . . . . . . . . . . | . . . . . . . . . . | . . . . . . . . . . | . . . . . . . . . . |
| Strain Zs7 {X16467} | . . . . . . . . . . | . . . . . . . . . . | . . . . . . . . . . | . . . . . . . . . . | . . . . . . . . . . | . . . . . . . . . . | . . . . . . . . . . |
| Strain B31 {X14407} | gagtca ttg | gttctcaaa | ag aaaa | g ct | acc t | aag c c | ag |
| Strain 25015 {S88693} | . . . . . . . . . . | . . . . . . . . . . | . . . . . . . . . . | . . . . . . . . . . | . . . . . . . . . . | . . . . . . . . . . | . . . . . . . . . . |
| Strain Dn127 | . . . . . . . . . . | . . . . . . . . . . | . . . . . . . . . . | . . . . . . . . . . | . . . . . . . . . . | . . . . . . . . . . | . . . . . . . . . . |
| Strain Pko {S48322} | . . . . . . . . . . | . . . . . . . . . . | . . . . . . . . . . | . . . . . . . . . . | . . . . . . . . . . | . . . . . . . . . . | . . . . . . . . . . |
| Strain Vs461 {Z29087} | . . . . . . . . . . | . . . . . . . . . . | . . . . . . . . . . | . . . . . . . . . . | . . . . . . . . . . | . . . . . . . . . . | . . . . . . . . . . |
| Strain Pgau {X62387} | . . . . . . . . . . | . . . . . . . . . . | . . . . . . . . . . | . . . . . . . . . . | . . . . . . . . . . | . . . . . . . . . . | . . . . . . . . . . |
| Strain G25 {Z29086} | . . . . . . . . . . | . . . . . . . . . . | . . . . . . . . . . | . . . . . . . . . . | . . . . . . . . . . | . . . . . . . . . . | . . . . . . . . . . |
| Strain Goe2 {X60300} | cttcag agc | agaagactt | . . . . . . . . . . | gt tct t | tc tga | a tga a t | tt |
| Strain K48 {X62624} | . . . . . . . . . . | . . . . . . . . . . | . . . . . . . . . . | . . . . . . . . . . | . . . . . . . . . . | . . . . . . . . . . | . . . . . . . . . . |
| Strain Zq1 {X66065} | . . . . . . . . . . | . . . . . . . . . . | . . . . . . . . . . | . . . . . . . . . . | . . . . . . . . . . | . . . . . . . . . . | . . . . . . . . . . |
| Strain Pbi {S48323} | . . . . . . . . . . | . . . . . . . . . . | . . . . . . . . . . | . . . . . . . . . . | . . . . . . . . . . | . . . . . . . . . . | . . . . . . . . . . |
| Strain 19857 {X68059} | . . . . . . . . . . | . . . . . . . . . . | . . . . . . . . . . | . . . . . . . . . . | . . . . . . . . . . | . . . . . . . . . . | . . . . . . . . . . |
| Consensus | - - - - - -A- - - | - - - - - - - - - | -A | - - -A- - -T-AT | - -AA- - -T-G | - - -A-T-T- - | |

FIG. 1V

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

TTATGAAAAA ATATTTATTG GGAAT                                      25

(2) INFORMATION FOR SEQ ID NO:2:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:2:

CTTTAAGCTC AAGCTTGTCT ACTGT                                      25

(2) INFORMATION FOR SEQ ID NO:3:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:3:

ACTAATGTTT TGCCATCTTC T                                                  21

(2) INFORMATION FOR SEQ ID NO:4:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:4:

ATTGGGAATA GGTCTAATAT TAGCCT                                   26

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GCATGTAAGC AAAATGTTAG C                                        21

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AAACGCTAAA CAAGACCTTC CTG                                      23

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

AGCTTTGAGA GTTTCCTCTG TTATTGA                                  27

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

TTAATCGAGC TTCTGATGAT GCTGC                                    25

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

ATTTCGTCTG TAAGTTGCTC TATTTCAA                                 28

(2) INFORMATION FOR SEQ ID NO:10:

(i) SEQUENCE CHARACTERISTICS:
  (A) LENGTH: 23 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:10:

GGTCTAATAT TAGCCTTAAT AGC  23

(2) INFORMATION FOR SEQ ID NO:11:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:11:

CAATTAGATC GTACTTGC  18

(2) INFORMATION FOR SEQ ID NO:12:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:12:

CCCTCACTAA ACATACCT  18

(2) INFORMATION FOR SEQ ID NO:13:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:13:

ATCTGTTACC AGCATGTAAT  20

(2) INFORMATION FOR SEQ ID NO:14:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:14:

GTTTTGTAAT TTCAACTGCT GACC  24

(2) INFORMATION FOR SEQ ID NO:15:

(i) SEQUENCE CHARACTERISTICS:

(A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CTGCAGCTTG GAATTCAGGC ACTTC                                                25

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GCCATTTGAG TCGTATTGTT GTACTG                                               26

(2) INFORMATION FOR SEQ ID NO:17:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GATTGAAGTC TGAAACTCCG ACTTCATGAA GTTGGAATCG CTAGTAAT                       48

(2) INFORMATION FOR SEQ ID NO:18:

(i) SEQUENCE CHARACTERISTICS:
        (A) LENGTH: 819 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:18:

ATGAAAAAAT ATTTATTGGG AATAGGTCTA ATATTAGCCT TAATAGCATG TAAGCAAAAT           60

GTTAGCAGCC TTGACGAGAA AAACAGCGTT TCAGTAGATT TGCCTGGTGA AATGAACGTT          120

CTTGTAAGCA AGAAAAAAA CAAAGACGGC AAGTACGATC TAATTGCAAC AGTAGACAAG           180

CTTGAGCTTA AGGAACTTC TGATAAAAAC AATGGATCTG GAGTACTTGA AGGCGTAAAA           240

GCTGACAAAA GTAAAGTAAA ATTAACAATT TCTGACGATC TAGGTCAAAC CACACTTGAA          300

GTTTTCAAAG AAGATGGCAA ACACTAGTA TCAAAAAAAG TAACTTCCAA AGACAAGTCA           360

TCAACAGAAG AAAAATTCAA TGAAAAAGGT GAAGTATCTG AAAAAATAAT AACAAGAGCA          420

GACGGAACCA GACTTGAATA CACAGAAATT AAAAGCGATG GATCTGGAAA AGCTAAAGAG          480

GTTTTAAAAG GCTATGTTCT TGAAGGAACT TTAACTGCTG AAAAAACAAC ATTGGTGGTT          540

AAAGAAGGAA CTGTTACTTT AAGCAAAAAT ATTTCAAAAT CTGGGGAAGT TTCAGTTGAA          600

CTTAATGACA CTGACAGTAG TGCTGCTACT AAAAAAACTG CAGCTTGGAA TTCAGGCACT          660

TCAACTTTAA CAATTACTGT AAACAGTAAA AAAACTAAAG ACCTTGTGTT TACAAAAGAA          720

AACACAATTA CAGTACAACA ATACGACTCA AATGGCACCA AATTAGAGGG GTCAGCAGTT          780

GAAATTACAA AACTTGATGA AATTAAAAAC GCTTTAAAA 819

(2) INFORMATION FOR SEQ ID NO:19:

(i) SEQUENCE CHARACTERISTICS:
        (A) LENGTH: 942 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:19:

```
CCAAACTTAA TTGAAGTTAT TATCATTTTA TTTTTTTTCA ATTTTCTATT TGTTATTTGT      60
TAATCTTATA ATATAATTAT ACTTGTATTA AGTTATATTA ATATAAAAGG AGAATATATT     120
ATGAAAAAAT ATTTATTGGG AATAGGTCTA ATATTAGCCT AATAGCATG TAAGCAAAAT      180
GTTAGCAGCC TTGACGAGAA AAACAGCGTT TCAGTAGATT TGCCTGGTGA AATGAACGTT     240
CTTGTAAGCA AGAAAAAAA CAAAGACGGC AAGTACGATC TAATTGCAAC AGTAGACAAG      300
CTTGAGCTTA AAGGAACTTC TGATAAAAAC AATGGATCTG GAGTACTTGA AGGCGTAAAA     360
GCTGACAAAA GTAAAGTAAA ATTAACAATT TCTGACGATC TAGGTCAAAC CACACTTGAA     420
GTTTTCAAAG AAGATGGCAA AACACTAGTA TCAAAAAAAG TAACTTCCAA AGACAAGTCA     480
TCAACAGAAG AAAAATTCAA TGAAAAAGGT GAAGTATCTG AAAAAATAAT AACAAGAGCA     540
GACGGAACCA GACTTGAATA CACAGAAATT AAAAGCGATG GATCTGGAAA AGCTAAAGAG     600
GTTTTAAAAA GCTATGTTCT TGAAGGAACT TTAACTGCTG AAAAAACAAC ATTGGTGGTT     660
AAAGAAGGAA CTGTTACTTT AAGCAAAAAT ATTTCAAAAT CTGGGGAAGT TTCAGTTGAA     720
CTTAATGCAA CTGACAGTAG TGCTGCTACT AAAAAAACTG CAGCTTGGAA TTCAGGCACT     780
TCAACTTTAA CAATTACTGT AAACAGTAAA AAAACTAAAG ACCTTGTGTT TACAAAAGAA     840
AACACAATTA CAGTACAACA ATACGACTCA AATGGCACCA AATTAGAGGG GTCAGCAGTT     900
GAAATTACAA AACTTGATGA AATTAAAAAC GCTTTAAAAT AA                        942
```

(2) INFORMATION FOR SEQ ID NO:20:

(i) SEQUENCE CHARACTERISTICS:
        (A) LENGTH: 1094 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:20:

```
AAGCTTAATT AGAACCAAAC TTAATTAAAA CCAAACTTAA TTGAAGTTAT TATCATTTTA      60
TTTTTTTCA ATTTTCTATT TGTTATTTGT TAATCTTATA ATATAATTAT ACTTGTATTA     120
AGTTATATTA ATATAAAAGG AGAATATATT ATGAAAAAAT ATTTATTGGG AATAGGTCTA     180
ATATTAGCCT AATAGCATG TAAGCAAAAT GTTAGCAGCC TTGACGAGAA AAACAGCGTT      240
TCAGTAGATT TGCCTGGTGA AATGAAAGTT CTTGTAAGCA AGAAAAAAA CAAAGACGGC      300
AAGTACGATC TAATTGCAAC AGTAGACAAG CTTGAGCTTA AAGGAACTTC TGATAAAAAC     360
AATGGATCTG GAGTACTTGA AGGCGTAAAA GCTGACAAAA GTAAAGTAAA ATTAACAATT     420
TCTGACGATC TAGGTCAAAC CACACTTGAA GTTTTCAAAG AAGATGGCAA AACACTAGTA     480
TCAAAAAAAG TAACTTCCAA AGACAAGTCA TCAACAGAAG AAAAATTCAA TGAAAAAGGT     540
```

```
GAAGTATCTG AAAAAATAAT AACAAGAGCA GACGGAACCA GACTTGAATA CACAGGAATT        600

AAAAGCGATG GATCTGGAAA AGCTAAAGAG GTTTTAAAAG GCTATGTTCT TGAAGGAACT        660

CTAACTGCTG AAAAAACAAC ATTGGTGGTT AAAGAAGGAA CTGTTACTTT AAGCAAAAAT        720

ATTTCAAAAT CTGGGGAAGT TTCAGTTGAA CTTAATGACA CTGACAGTAG TGCTGCTACT        780

AAAAAAACTG CAGCTTGGAA TTCAGGCACT TCAACTTTAA CAATTACTGT AAACAGTAAA        840

AAAACTAAAG ACCTTGTGTT TACAAAAGAA AACACAATTA CAGTACAACA ATACGACTCA        900

AATGGCACCA AATTAGAGGG GTCAGCAGTT GAAATTACAA AACTTGATGA AATTAAAAAC        960

GCTTTAAAAT AAGGAGAATT TATGAGATTA TTAATAGGAT TTGCTTTAGC GTTAGCTTTA       1020

ATAGGATGTG CACAAAAAGG TGCTGAGTCA ATTGGTTCTC AAAAAGAAAA TGATCTAAAC       1080

CTTGAAGACT CTGA                                                        1094

(2) INFORMATION FOR SEQ ID NO:21:

(i) SEQUENCE CHARACTERISTICS:
        (A) LENGTH: 819 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:21:

ATGAAAAAAT ATTTATTGGG AATAGGTCTA ATATTAGCTT TAATAGCATG TAAGCAAAAT         60

GTTAGCAGCC TTGACGAGAA AAACAGCGTT TCAGTAGATT TGCCTGGTGA AATGAAAGTT        120

CTTGTAAGCA AAGAAAAAGA CAAAGACGGC AAGTACAGTC TAATGGCAAC AGTAGACAAG        180

CTTGAGCTTA AAGGAACATC TGATAAAAAC AATGGATCTG GGGTGCTTGA AGGCGTAAAA        240

GCTGACAAAA GCAAAGTAAA ATTAACAGTT TCTGACGATC TAAGCACAAC CACACTTGAA        300

GTTTTAAAAG AAGATGGCAA AACATTAGTG TCAAAAAAAA GAACTTCTAA AGATAAGTCA        360

TCAACAGAAG AAAAGTTCAA TGAAAAAGGC GAATTAGTTG AAAAAAATAA TGGCAAGAGCA       420

AACGGAACCA TACTTGAATA CACAGGAATT AAAAGCGATG GATCCGGAAA AGCTAAAGAA        480

ACTTTAAAAG AATATGTTCT TGAAGGAACT CTAACTGCTG AAAAAGCAAC ATTGGTGGTT        540

AAAGAAGGAA CTGTTACTTT AAGTAAGCAC ATTTCAAAAT CTGGAGAAGT AACAGCTGAA        600

CTTAATGACA CTGACAGTAC TCAAGCTACT AAAAAAACTG GGAAATGGGA TGCAGGCACT        660

TCAACTTTAA CAATTACTGT AAACAACAAA AAAACTAAAG CCCTTGTATT TACAAAACAA        720

GACACAATTA CATCACAAAA ATACGACTCA GCAGGAACCA ACTTGGAAGG CACAGCAGTC        780

GAAATTAAAA CACTTGATGA ACTTAAAAAC GCTTTAAGA                              819

(2) INFORMATION FOR SEQ ID NO:22:

(i) SEQUENCE CHARACTERISTICS:
        (A) LENGTH: 615 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:22:

AAAAACAATG GATCTGGGAT ACTTGAAGGC GTAAAAGCTG ACAAAAGCAA AGTAAAATTA         60

ACAGTTTCTG AGGATCTCAG CACAACTACA CTTGAAGTTC TAAAAGAAGA TGGCAAAACA        120

TTGGTGTCAA AAAAACAAC TTCTAAAGAC AAGTCATCAA CAGAAGAAAA GTTCAATGCA        180
```

```
AAGGCGAATT AGCTGAAAAA ACAATAGTAA GAGCAAACGG AACCAGACTT GAATACACAG        240

AAGTTAAAAG CGATGGATCC GGAAAAGCTA AAGAAACTTT AAAAGACTAT GCTGTTGAAG        300

GAACTCTAAC TGCTGAAAAA GCAACATTGG TGGTTAAAGA AGGAACTGTT ACTTTAAGTA        360

AGCACATTTC AAAATCCGGA GAAGTAACAG CTGAGCTTAA TGACACTGAC TGTGCTCAAG        420

CTACTAAAAA AACTGGAAAA TGGGATGCGG GAACTTCAAC TTTAACAATT AGCGTAAACA        480

GCAAAAAAAC TAAAAACCTT GTATTTACAA AACAAGACAC AATTACAGTA CAAAAATACG        540

ACTCAGCAGG CACCAACTTG GAAGGCACAG CAGTCGAAAT TAAAACACTT GATGAACTTA        600

AAAACGCTTT AAAAT                                                         615
```

(2) INFORMATION FOR SEQ ID NO:23:

(i) SEQUENCE CHARACTERISTICS:
        (A) LENGTH: 892 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:23:

```
TATACTATAA TATACTATAA TTATACTTGT ATTAAGTTAT ATTAATATAA TATAAAAAGG         60

AGAATATATT ATGAAAAAAT ATTTATTGGG AATAGGTCTA ATATTAGCCT TAATAGCATG        120

CAAGCAAAAT GTTAGCAGCC TTGATGAAAA AAACAGCGCT TCAGTAGATT TGCCTGGTGA        180

GATGAAAGTT CTTGTAAGTA AAGAAAAAGA CAAAGACGGT AAGTACAGTC TAAAGGCAAC        240

AGTAGACAAG ATTGAGCTAA AAGGAACTTC TGATAAAGAC AATGGTTCTG GGGTGCTTGA        300

AGGTACAAAA GATGACAAAA GTAAAGCAAA ATTAACAATT GCTGACGATC TAAGTAAAAC        360

CACATTCGAA CTTTTCAAAG AAGATGGCAA AACATTAGTG TCAAGAAAAG TAAGTTCTAA        420

AGACAAAACA TCAACAGATG AAATGTTCAA TGAAAAAGGT GAATTGTCTG CAAAAACCAT        480

GACAAGAGAA AATGGAACCA AACTTGAATA TACAGAAATG AAAAGCGATG GAACCGGAAA        540

AGCTAAAGAA GTTTTAAAAA ACTTTACTCT TGAAGGAAAA GTAGCTAATG ATAAAGTAAC        600

ATTGGAAGTA AAAGAAGGAA CCGTTACTTT AAGTAAGGAA ATTGCAAAAT CTGGAGAAGT        660

AACAGTTGCT CTTAATGACA CTAACACTAC TCAGGCTACT AAAAAAACTG GCGCATGGGA        720

TTCAAAAACT TCTACTTTAA CAATTAGTGT TAACAGCAAA AAAACTACAC AACTTGTGTT        780

TACTAAACAA GACACAATAA CTGTACAAAA ATACGACTCC GCAGGTACCA ATTTAGAAGG        840

CACAGCAGTC GAAATTAAAA CACTTGATGA ACTTAAAAAC GCTTTGAAAT AA              892
```

(2) INFORMATION FOR SEQ ID NO:24:

(i) SEQUENCE CHARACTERISTICS:
        (A) LENGTH: 822 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:24:

```
ATGAAAAAAT ATTTATTGGG AATAGGTCTA ATATTAGCCT TAATAGCATG CAAGCAAAAT         60

GTTAGCAGCC TTGATGAAAA AAACAGCGCT TCAGTAGATT TGCCTGGTGA GATGAAAGTT        120

CTTGTAAGTA AAGAAAAAGA CAAAGACGGT AAGTACAGTC TAAAGGCAAC AGTAGACAAG        180
```

```
ATTGAGCTAA AAGGAACTTC TGATAAAGAC AATGGTTCTG GAGTGCTTGA AGGTACAAAA      240

GATGACAAAA GTAAAGCAAA ATTAACAATT GCTGACGATC TAAGTAAAAC CACATTCGAA      300

CTTTTCAAAG AAGATGGCAA AACATTAGTG TCAAGAAAAG TAAGTTCTAA AGACAAAACA      360

TCAACAGATG AAATGTTCAA TGAAAAAGGT GAATTGTCTG CAAAAACCAT GACAAGAGAA      420

AATGGAACCA AACTTGAATA TACAGAAATG AAAAGCGATG GAACCGGAAA AGCTAAAGAA      480

GTTTTAAAAA ACTTTACTCT TGAAGGAAAA GTAGCTAATG ATAAAGTAAC ATTGGAAGTA      540

AAAGAAGGAA CCGTTACTTT AAGTAAGGAA ATTGCAAAAT CTGGAGAAGT AACAGTTGCT      600

CTTAATGACA CTAACACTAC TCAGGCTACT AAAAAAACTG GCGCATGGGA TTCAAAAACT      660

TCTACTTTAA CAATTAGTGT TAACAGCAAA AAAACTACAC AACTTGTGTT TACTAAACAA      720

GACACAATAA CTGTACAAAA ATACGACTCC GCAGGTACCA ATTTAGAAGG CACAGCAGGC      780

GAAATTAAAA CACTTGATGA ACTTAAAAAC GCTTTGAAAT AA                        822

(2) INFORMATION FOR SEQ ID NO:25:

(i) SEQUENCE CHARACTERISTICS:
         (A) LENGTH: 822 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:25:

ATGAAAAAAT ATTTATTGGG AATAGGTCTA ATATTAGCCT TAATAGCATG CAAGCAAAAT       60

GTTAGCAGCC TTGATGAAAA AAACAGCGCT TCAGTAGATT TGCCTGGTGA GATGAAAGTT      120

CTTGTAAGTA AAGAAAAGA CAAAGACGGT AAGTACAGTC TAAAGGCAAC AGTAGACAAG       180

ATTGAGCTAA AAGGAACTTC TGATAAAGAC AATGGTTCTG GAGTGCTTGA AGGTACAAAA      240

GATGACAAAA GTAAAGCAAA ATTAACAATT GCTGACGATC TAAGTAAAAC CACATTCGAA      300

CTTTTAAAAG AAGATGGCAA AACATTAGTG TCAAGAAAAG TAAGTTCTAG AGACAAAACA      360

TCAACAGATG AAATGTTCAA TGAAAAAGGT GAATTGTCTG CAAAAACCAT GACAAGAGAA      420

AATGGAACCA AACTTGAATA TACAGAAATG AAAAGCGATG GAACCGGAAA AGCTAAAGAA      480

GTTTTAAAAA AGTTTACTCT TGAAGGAAAA GTAGCTAATG ATAAAGTAAC ATTGGAAGTA      540

AAAGAAGGAA CCGTTACTTT AAGTAAGGAA ATTGCAAAAT CTGGAGAAGT AACAGTTGCT      600

CTTAATGACA CTAACACTAC TCAGGCTACT AAAAAAACTG GCGCATGGGA TTCAAAAACT      660

TCTACTTTAA CAATTAGTGT TAACAGCAAA AAAACTACAC AACTTGTGTT TACTAAACAA      720

TACACAATAA CTGTAAAACA ATACGACTCC GCAGGTACCA ATTTAGAAGG CACAGCAGTC      780

GAAATTAAAA CACTTGATGA ACTTAAAAAC GCTTTAAAAT AA                        822

(2) INFORMATION FOR SEQ ID NO:26:

(i) SEQUENCE CHARACTERISTICS:
         (A) LENGTH: 825 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:26:

ATGAAAAAAT ATTTATTGGG AATAGGTCTA ATATTAGCCT TAATAGCATG TAAGCAAAAT       60

GTTAGCAGCC TTGATGAAAA AAATAGCGTT TCAGTAGATT TACCTGGTGG AATGACAGTT      120
```

-continued

```
CTTGTAAGTA AAGAAAAAGA CAAAGACGGT AAATACAGTC TAGAGGCAAC AGTAGACAAG      180

CTTGAGCTTA AAGGAACTTC TGATAAAAAC AACGGTTCTG GAACACTTGA AGGTGAAAAA      240

ACTGACAAAA GTAAAGTAAA ATTAACAATT GCTGATGACC TAAGTCAAAC TAAATTTGAA      300

ATTTTCAAAG AAGATGGCAA ACATTAGTA TCAAAAAAG TAACCCTTAA AGACAAGTCA        360

TCAACAGAAG AAAAATTCAA CGAAAAGGGT GAAACATCTG AAAAACAAT AGTAAGAGCA       420

AATGGAACCA GACTTGAATA CACAGACATA AAAAGCGATG GATCCGGAAA AGCTAAAGAA      480

GTTTTAAAAG ACTTTACTCT TGAAGGAACT CTAGCTGCTG ACGGCAAAAC AACATTGAAA      540

GTTACAGAAG GCACTGTTGT TTTAAGCAAG AACATTTTAA ATCCGGAGA ATAACAGTT        600

GCACTTGATG ACTCTGACAC TACTCAGGCT ACTAAAAAAA CTGGAAAATG GGATTCAAAG      660

ACTTCCACTT TAACAATTAG TGTGAATAGC CAAAAAACCA AAAACCTTGT ATTCACAAAA      720

GAAGACACAA TAACAGTACA AAAATACGAC TCAGCAGGCA CCAATCTAGA AGGCAAAGCA      780

GTCGAAATTA CAACACTTAA AGAACTTAAA GACGCTTTAA AATAA                      825
```

(2) INFORMATION FOR SEQ ID NO:27:

(i) SEQUENCE CHARACTERISTICS:
        (A) LENGTH: 1089 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:27:

```
AAAAGTTTAT ATTTGTTCTA TATCTAATTT AGAATTATTA TCATTTTATT TTTTTTCAAT      60

TTTCTATTTG TTATTTGTTG ATCTTATACT ATAATTATAT TTGTATTAAG TTATATTAAT     120

ATAATATAAA AAGGAGAATA TATTATGAAA AAATATTTAT TGGGAATAGG TCTAATATTA     180

GCCTTAATAG CATGTAAGCA AAATGTTAGC AGCCTTGATG AAAAAAATAG CGTTTCAGTA     240

GATTTACCTG GTGGAATGAC AGTTCTTGTA AGTAAAGAAA AAGACAAAGA CGGTAAATAC     300

AGTCTAGAGG CAACAGTAGA CAAGCTTGAG CTTAAAGGAA CTTCTGATAA AAACAACGGT     360

TCTGGAACAC TTGAAGGTGA AAAAACTGAC AAAAGTAAAG TAAAATTAAC AATTGCTGAT     420

GACCTAAGTC AAACTAAATT TGAAATTTTC AAAGAAGATG GCAAAACATT AGTATCAAAA     480

AAAGTAACCC TTAAAGACAA GTCATCAACA GAAGAAAAAT TCAACGAAAA GGGTGAAACA     540

TCTGAAAAAA CAATAGTAAG AGCAAATGGA ACCAGACTTG AATACACAGA CATAAAAAGC     600

GATGGATCCG GAAAAGCTAA AGAAGTTTTA AAAGACTTTA CTCTTGAAGG AACTCTAGCT     660

GCTGACGGCA AAACAACATT GAAAGTTACA GAAGGCACTG TTGTTTTAAG CAAGAACATT     720

TTAAAATCCG GAGAAATAAC AGTTGCACTT GATGACTCTG ACACTACTCA GGCTACTAAA     780

AAAACTGGAA AATNGGATTC AAAGACTTCC ACTTTAACAA TTAGTGTGAA TAGCCAAAAA     840

ACCAAAAACC TTGTATTCAC AAAAGAAGAC ACAATAACAG TACAAAAATA CGACTCAGCA     900

GGCACCAATC TAGAAGGCAA AGCAGTCGAA ATTACAACAC TTAAAGAACT TAAAGACGCT     960

TTAAAATAAG GAGAATTTAT GAAACAATAT TTACCGTTTT AAACACTAGC AAAACAGAAA    1020

AATATTTGAA CAAAAATCTT CCTTCAGAAG CAGAAGACTT GTATCTTTAT TCAATGATAT    1080

GAAATTTTT                                                            1089
```

(2) INFORMATION FOR SEQ ID NO:28:

(i) SEQUENCE CHARACTERISTICS:
    (A) LENGTH: 825 base pairs
    (B) TYPE: nucleic acid
    (C) STRANDEDNESS: single
    (D) TOPOLOGY: linear (ii) MOLECULE TYPE: Genomic DNA (xi) SEQUENCE DESCRIPTION: SEQ ID NO:28:

```
ATGAAAAAAT ATTTATTGGG AATAGGTCTA ATATTAGCCT TAATAGCATG TAAGCAAAAT      60
GTTAGCACGC TTGATGAAAA AAATAGCGTT TCAGTAGATT TACCTGGTGG AATGACAGAA     120
CTTGTAAGTA AAGAAAAAGA CAAAGACGGT AAATACAGTC TAGAGGCAAC AGTAGACAAG     180
CTTGAGCTTA AAGGAACTTC TGATAAAAAC AACGGTTCTG GAACACTTGA AGGTGAAAAA     240
ACTGACAAAA GTAAAGTAAA ATTAACAATT GCTGATGACC TAAGTCAAAC TAAATTTGAA     300
ATTTTCAAAG AAGATGCCAA ACATTAGTA TCAAAAAAAG TAACCCTTAA AGACAAGTCA      360
TCAACAGAAG AAAAATTCAA CGAAAAGGGT GAAACATCTG AAAAAACAAT AGTAAGAGCA     420
AATGGAACCA GACTTGAATA CACAGACATA AAAAGCGATG GATCCGGAAA AGCTAAAGAA     480
GTTTTAAAAG ACTTTACTCT TGAAGGAACT CTAGCTGCTG ACGGCAAAAC AACATTGAAA     540
GTTACAGAAG GCACTGTTGT TTTAAGCAAG AACATTTTAA ATCCGGAGA AATAACAGTT      600
GCACTTGATG ACTCTGACAC TACTCAGGCT ACTAAAAAAA CTGGAAAATG GGATTCAAAA     660
ACTTCCACTT TAACAATTAG TGTGAATAGC CAAAAAACCA AAAACCTTGT ATTCACAAAA     720
GAAGACACAA TAACAGTACA AAAATACGAC TCAGCAGGCA CCAATCTAGA AGGCAAAGCA     780
GTCGAAATTA CAACACTTAA AGAACTTAAA AACGCTTTAA AATAA                     825
```

(2) INFORMATION FOR SEQ ID NO:29:

(i) SEQUENCE CHARACTERISTICS:
    (A) LENGTH: 825 base pairs
    (B) TYPE: nucleic acid
    (C) STRANDEDNESS: single
    (D) TOPOLOGY: linear (ii) MOLECULE TYPE: Genomic DNA (xi) SEQUENCE DESCRIPTION: SEQ ID NO:29:

```
ATGAAAAAAT ATTTATTGGG AATAGGTCTA ATATTAGCCT TAATAGCATG TAAGCAAAAT      60
GTTAGCAGCC TTGATGAAAA AAATAGCGTT TCAGTAGATT TACCTGGTGG AATGAAAGTT     120
CTTGTAAGTA AAGAAAAAGA CAAAGATGGT AAATACAGTC TAGAGGCAAC AGTAGACAAG     180
CTTGAGCTTA AAGGAACTTC TGATAAAAAC AACGGTTCTG GAACACTTGA AGGTGAAAAA     240
ACTGACAAAA GTAAAGTAAA ATTAACAATT GCTGAGGATC TAAGTAAAAC CACATTTGAA     300
ATTTTCAAAG AAGATGGCAA ACATTAGTA TCAAAAAAAG TAACCCTTAA AGACAAGTCA      360
TCAACAGAAG AAAAATTCAA CGAAAAGGGT GAAATATCTG AAAAAACAAT AGTAAGAGCA     420
AATGGAACCA GACTTGAATA CACAGACATA AAAAGCGATG GATCCGGAAA AGCTAAAGAA     480
GTTTTAAAAG ACTTTACTCT TGAAGGAACT CTAGCTGCTG ACGGCAAAAC AACATTGAAA     540
GTTACAGAAG GCACTGTTGT TTTAAGCAAG AACATTTTAA ATCCGGAGA AATAACAGTT      600
GCACTTGATG ACTCTGACAC TACTCAGGCT ACTAAAAAAA CTGGAAAATG GGATTCAAAG     660
ACTTCCACTT TAACAATTAG TGTGAATAGC CAAAAAACCA AAAACCTTGT ATTCACAAAA     720
GAAGACACAA TAACAGTACA AAAATACGAC TCAGCAGGCA CCAATCTAGA AGGCAAAGCA     780
GTCGAAATTA CAACACTTAA AGAACTTAAA GACGCTTTAA AATAA                     825
```

(2) INFORMATION FOR SEQ ID NO:30:

(i) SEQUENCE CHARACTERISTICS:
        (A) LENGTH: 839 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:30:

```
GGATCCATCA TGAAAAAATA TTTATTGGGA ATAGGTCTAA TATTAGCCTT AATAGCATGT      60

AAGCAAAATG TTAGCAGCCT TGATGAGAAA AACAGCGTTT CAGTAGATTT ACCTGGTGAA     120

ATGAAAGTTC TTGTAAGCAA AGAAAAAGAC AAAGATGGTA AATACAGTCT AATGGCAACA     180

GTAGACAAGC TAGAGCTTAA AGGAACTTCT GATAAAAGCA ACGGTTCTGG AACACTTGAA     240

GGTGAAAAAT CTGACAAAAG TAAAGCAAAA TTAACAATTT CTGAAGATCT AAGTAAAACC     300

ACATTTGAAA TTTTCAAAGA AGATGGCAAA ACATTAGTAT CAAAAAAGT AAATTCTAAA      360

GATAAGTCAT CAATAGAAGA AAAATTCAAC GCAAAAGGTG AATTATCTGA AAAAACAATA     420

CTAAGAGCAA ACGGAACCAG GCTTGAATAC ACAGAAATAA AAGCGATGG AACCGGAAAA      480

GCTAAAGAAG TTTTAAAAGA CTTTGCTCTT GAAGGAACTC TAGCTGCCGA CAAAACAACA     540

TTGAAAGTTA CAGAAGGCAC TGTTGTTTTA AGCAAACACA TTCCAAACTC TGGAGAAATA     600

ACAGTTGAGC TTAATGACTC TAACTCTACT CAGGCTACTA AAAAAACTGG AAAATGGGAT     660

TCAAATACTT CCACTTTAAC AATTAGTGTG AATAGCAAAA AAACTAAAAA CATTGTATTT     720

ACAAAAGAAG ACACAATAAC AGTACAAAAA TACGACTCAG CAGGCACCAA TCTAGAAGGC     780

AACGCAGTCG AAATTAAAAC ACTTGATGAA CTTAAAAACG CTTTAAAATA AGAGAATTC     839
```

(2) INFORMATION FOR SEQ ID NO:31:

(i) SEQUENCE CHARACTERISTICS:
        (A) LENGTH: 819 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:31:

```
ATGAAAAAAT ATTTATTGGG AATAGGTCTA ATATTAGCCT TAATAGCATG TAAGCAAAAT      60

GTTAGCAGCC TTGACGAGAA AAACAGCGTT TCAGTAGATG TACCTGGTGG AATGAAAGTT     120

CTTGTAAGCA AGAAAAAAA CAAAGACGGC AAGTACGATC TAATGGCAAC AGTGGACAAC      180

GTTGATCTTA AGGAACTTC TGACAAAAAC AATGGATCTG GAATACTTGA AGGCGTAAAA      240

GCTGATAAAA GTAAAGTAAA ATTAACAGTT GCTGACGATC TAAGCAAAAC CACACTTGAA     300

GTTTTAAAAG AAGATGGTAC AGTAGTGTCA AGAAAAGTAA CTTCCAAAGA CAAGTCAACA     360

ACAGAAGCAA AATTCAACGA AAAAGGTGAA TTGTCTGAAA AACAATGAC AAGAGCAAAC      420

GGAACTACTC TTGAATACTC ACAAATGACA AATGAAGACA ATGCTGCAAA AGCAGTAGAA     480

ACTCTTAAAA ACGGCATTAA GTTTGAAGGA ATCTCGCAA GTGGAAAAAC AGCAGTGGAA      540

ATTAAAGAAG GCACTGTTAC TCTAAAAAGA GAAATTGATA AAAATGGAAA AGTAACCGTC     600

TCTTTAAATG ACACTGCATC TGGTTCTAAA AAAACAGCTT CCTGGCAAGA AAGTACTAGC     660

ACCTTAACAA TTAGTGCAAA CAGCAAAAAA ACTAAAGATC TAGTGTTCCT AACAAACGGT     720

ACAATTACAG TACAAAATTA TGACTCAGCT GGCACTAAAC TTGAAGGATC AGCAGCTGAA     780
```

-continued

```
ATTAAAAAAC TCGATGAACT TAAAAACGCT TTAAGATAA                              819
```

(2) INFORMATION FOR SEQ ID NO:32:

(i) SEQUENCE CHARACTERISTICS:
        (A) LENGTH: 1100 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:32:

```
NNNNNNAANN NNNNNNANNN NTNNTNNANN CCAAACTTAA TTGAAGTTAT TATCATTTTA         60

TTTTTTTTCA ATTTTCTATT TGTTATTTGT TANNCTNNNA NTATAATTNT ANTNNNNTNN        120

ANTNATATNA NNNNAAAAGG AGAATATATT ATGAAAAAAT ATTTATTGGG AATAGGTCTA        180

ATATTAGCCT TAATAGCATG TAAGCAAAAT GTTAGCAGCC TTGATGAAAA AAACAGCGTT        240

TCAGTAGATT TGCCTGGTGA AATGAAAGTT CTTGTAAGTA AAGAAAAAGA CAAAGACGGT        300

AAGTACAGTC TAAAGGCAAC AGTAGACAAG CTTGAGCTTA AAGGAACTTC TGATAAAAAC        360

AATGGTTCTG GANTACTTGA AGGTGTAAAA GCTGACAAAA GTAAAGTAAA ATTAACAATT        420

GCTGACGATC TAAGTAAAAC CACATTTGAA GTTTTCAAAG AAGATGGCAA AACATTAGTA        480

TCAAAAAAAG TAACTTCTAA AGACAAGTCA TCAACAGAAG AAAAATTCAA TGAAAAAGGT        540

GAATTATCTG AAAAAACAAT AACAAGAGCA AANGGAACCA GACTTGAATA CACAGAAATN        600

AAAAGCGATG GATNNNCCGG AAAAGCTAAA GAAGTTTTAA AAGACTTTAC TCTTGAAGGA        660

ACTCTAGCTG CTGACGGAAA AACAACATTG GAAGTTAAAG AAGGAACTGT TACTTTAAGC        720

AAGAACATTT CAAAATCTGG AGAAGTAACA GTTGCACTTA ATGACACTGA CACTACTCAG        780

GCTACTAAAA AAACTGGAAN ATGGGATTCA AAAACTTCCA CTTTAACAAT TAGTGTAAAC        840

AGCAAAAAAA CTAAAAACCT TGTNTTTACA AAAGAAGACA CAATAACAGT ACAAAAATAC        900

GACTCAGCAG GCACCAATTT AGAAGGCACA GCAGTCGAAA TTANAACACT TGATGAACTT        960

AAAAACGCTT TAAAATAAGG AGAATTTATG ANANNATNNN TANNNTTTNN NNNANNNNNA       1020

NNNNNNANAN NNNNTNNANN AAAANNNNNN NNNNNNANNN NNNNNNNNNA NNANNNTNAT       1080

NNAANNNTNG NNNNANTNTNN                                                 1100
```

PCR DETECTION OF *BORRELIA BURGDORFERI*

This is a continuation of application Ser. No. 08/241,496, filed May 12, 1994 now abandoned.

STATEMENT OF GOVERNMENT RIGHTS

The present invention was made with the support of the National Institutes of Health under Grant Nos. AI30548 and AR41497. The Government has certain rights to this invention.

BACKGROUND OF THE INVENTION

Lyme borreliosis (Lyme disease), a systemic illness with a wide spectrum of clinical symptoms, was named for Lyme, Conn., where the disease was identified. Although subsets of the diverse clinical manifestations of Lyme disease were recorded in Europe early in this century, recognition of the disease as a distinct clinical entity did not occur until the mid-1970s. Today, Lyme disease is the most common tick-borne zoonosis in the United States, with more than 6000 human infections reported each year.

Lyme disease is a multisystem disorder with dermatologic, neurologic and musculoskeletal components that is caused by the spirochete *Borrelia burgdorferi*. The risk of a human acquiring Lyme disease is dependent on an interplay of microbial, environmental, and demographic factors. Ultimately, transmission is effected by nymphal ticks of the *Ixodes ricinus* complex. Illness usually develops three to thirty days following the tick bite, and often begins with a primary skin lesion called erythema migrans, followed by cardiac, neurologic, or arthritic symptoms. These resulting symptoms vary in severity, are disease stage dependent, and often mimic other conditions. This multifaceted presentation often delays and confuses clinical diagnosis.

Currently bacterial culture and serologic methods are used in diagnosis. See, A. C. Steere, *N. Engl. J. Med.*, 321, 568–596 (1989). In the early stages of Lyme disease, *B. burgdorferi* can be readily recovered by culture from biopsy specimens of the erythema migrans skin lesions. P. D. Mitchell et al., *Am. J. Clin. Pathol.*, 99, 104 (1993). However, as the disease progresses, the organism becomes increasingly difficult to detect by culture. In addition, limited sensitivity and specificity and lack of test standardization between laboratories have hindered the interpretation of results.

The inadequacy of current diagnostic techniques is well-illustrated by the difficulties encountered in confirming diagnosis in patients with suspected Lyme arthritis, a late manifestation of Lyme disease that results in episodic synovial inflammation and swelling. In these patients, successful cultivation of spirochetes from synovial (joint) fluid specimens has been reported only twice. Lyme arthritis can usually be treated successfully with either a one-month course of doxycycline or amoxicillin or a two-week course of intravenous certriaxone or penicillin. In some patients, however, arthritis persists despite multiple courses of oral and intravenous antibiotic therapy. It has been unclear whether this treatment-resistant course results from persistent infection or from postinfective immune-mediated phenomena. The ability to demonstrate unequivocally the presence or absence of *B. burgdorferi* in the joint would improve the understanding of the pathogenesis of Lyme arthritis, and assist in identifying appropriate treatment protocols.

Detection of deoxyribonucleic acid (DNA) from *B. burgdorferi* in tissue and fluid specimens using the polymerase chain reaction (PCR) provides direct proof of continuing infection and is an important diagnostic tool. See, D. H. Persing, "Molecular detection of *Borrelia burgdorferi*," in S. Schutzer, ed. *Lyme Disease: Molecular and Immunologic Approaches*, Cold Spring Harbor, N.Y., Cold Spring Harbor Laboratory Press, 299–315 (1993). To date, genomic and plasmid DNA sequences from *B. burgdorferi* have been used as targets with limited success. For example, specific DNA sequences encoding the outer surface protein A (OSPA) present on the 54-kb plasmid in *B. burgdorferi* B31, along with the genomic sequences encoding the flagellin and 16S rDNA genes have been used as targets. See, D. H. Persing et al., *Science*, 249, 1420–1423 (1990); D. H. Persing et al., *J. Infect. Dis.*, 169, 668–672 (1994); S. L. Goodman et al., *Infect. Immun.*, 59, 269–278 (1991); and P. A. Rosa et al., *J. Infect. Dis.*, 160, 1018–1029 (1989). The range and quality of specimen types and collection and transport conditions have confounded attempts to design a single efficient standard processing technique; the varied physical characteristics and DNA content of the specimens, ranging from bacterial cultures, tick extracts, whole blood, serum, joint fluid, urine, and cerebrospinal fluid, require that protocols be developed for each specimen type to obtain a satisfactory yield of target DNA free from inhibitors that are often present. Moreover, genomic *B. bergdorferi* DNA is considerably more difficult than extrachromosomal DNA to detect in advanced cases of Lyme disease. D. H. Persing et al., *J. Infect. Dis.*, 169, 668–672 (1994). Furthermore, existing methods for detecting *B. burgdorferi* DNA using PCR are strictly experimental and have no proven clinical value. Thus, what is needed is a highly selective, specific, sensitive, and practical method for detecting genetic evidence of the Lyme-disease causing spirochete in a variety of clinical specimens at varying stages of the disease.

SUMMARY OF THE INVENTION

The present invention is directed to methods based on the polymerase chain reaction (PCR) for the detection of Lyme-disease causing spirochetes in biological samples, and unique primers used therein. These methods are direct methods for the detection of spirochete DNA, whether the spirochete is active or inactive (inactivated by treatment, for example, with an antibiotic), in a variety of biological samples, e.g., samples from arthropods, domestic animals, humans, etc. The methods of the present invention can be used to detect spirochete DNA in, for example, fluid samples such as whole blood, blood serum, cerebrospinal fluid, urine, synovial fluid, etc., and in tissue samples such as brain tissue and other neurological tissues, cardiac tissue, skin, lymph nodes, etc. The methods of the present invention are particularly advantageous because they have proven clinical value. That is, they show greater than 90% sensitivity and greater than 90% specificity, and often greater than 95% sensitivity and 100% specificity, particularly when used to detect Lyme-arthritis causing spirochetes in synovial fluid.

One method of the present invention for detecting in a biological sample the presence of Lyme-disease causing spirochetes using the polymerase chain reaction (PCR) includes the steps of: isolating DNA from the biological sample; amplifying the isolated DNA under hybridizing conditions with a primer pair that targets portions of extrachromosomal linear plasmid gene encoding outer surface protein A (OspA) of the Lyme-disease causing spirochetes, wherein said primer pair is derived from highly conserved portions of said OspA gene; probing said amplified DNA under hybridizing conditions with a labeled gene probe; and detecting the labeled gene probe that hybridized to said amplified DNA of the Lyme-disease causing spirochetes. Another embodiment of the present invention uses a primer pair and probe that targets portions of extrachromosomal linear plasmid gene encoding outer surface protein B (OspB) of the Lyme-disease causing spirochetes.

These methods are useful for detecting a variety of Lyme-disease causing spirochetes, particularly those of the genus Borrelia. Any of a variety of strains of Borrelia spirochetes can be detected, including, for example, those within the species classifications *Borrelia burgdorferi*, *Borrelia garnii*, and *Borrelia afzelii*, as well as a variety of as yet unclassified strains. Specific examples of such strains that can be detected with the methods of the present invention include, for example, CDC strains 89-1421, 90-1246, 90-1654, 90-2246, 90-2810, 91-1226, 91-1828, 92-0889, 92-0953, as well as strains CA4, CA7, CA8, CA9, B172, B31, DN127, and N40. On the other hand, the methods described herein are specific for Lyme-disease causing spirochetes; they do not detect members of the genus Borrelia that are not associated with Lyme-disease.

The methods of the present invention use standard PCR techniques, preferably modified to include the use of isopsoralen, i.e., a three-ring compound activated by UV light, in the PCR master mix used for amplification of isolated DNA. An amount of isopsoralen is used that is effective to inactivate the amplified product, i.e., stop the polymerization process. This helps avoid false positives.

The OspA primers used in the PCR methods are derived from several highly conserved portions of the extracellular linear plasmid OspA gene. As used herein, "highly conserved" means that these portions of the gene have at least about 75% sequence identity among DNA of 14 spirochete strains, based on multiple sequence analysis and alignment of OspA genes. For example, one useful primer preferably contains 15–93 nucleotides, more preferably 18–30 nucleotides, and hybridizes under hybridizing conditions to nucleotides 135–227 in the *Borrelia burgdorferi* consensus sequence shown in FIG. 1. This primer preferably substantially corresponds to the nucleotide sequence of primer OspA149, shown below in Table 1. As used herein, "substantially corresponds to" means that the primer sequence of interest has at least about 50% sequence identity with the referenced primer sequence. Most preferably, this primer is the primer referred to herein as OspA149. This primer can be used with either of the two following primers: a primer containing 15–56 nucleotides, preferably 18–30 nucleotides, that hybridizes under hybridizing conditions to nucleotides 316–371 in the *Borrelia burgdorferi* consensus sequence shown in FIG. 1 (preferably this primer substantially corresponds to primer OspA319, and more preferably is primer OspA319); and a primer containing 15–37 nucleotides, preferably 18–30 nucleotides, that hybridizes under hybridizing conditions to nucleotides 457–493 in the *Borrelia burgdorferi* consensus sequence shown in FIG. 1 (preferably this primer substantially corresponds to primer OspA459, and more preferably is primer OspA459). Thus, two particularly preferred primer pairs are primers OspA149 and OspA319, and primers OspA149 and OspA459. The OspB primers used in the PCR methods of the present invention substantially correspond to the primers referred to in Table 1 as OspB1110 and OspB1411. Preferably, these primers are OspB1110 and OspB1411.

The labeled probes used in the methods of the present invention include any useful probe that hybridizes to the amplified products under hybridizing conditions. Such probes can be internal oligonucleotide probes, either synthetic or naturally occurring, an amplification product, or a plasmid or portion thereof containing an amplification product or a portion thereof. Preferred probes are those substantially corresponding to the probes listed in Table 1 below. More preferred probes are those listed in Table 1. The probes can be labeled with any standard detectable label, such as $^{32}$P, $^{33}$P, $^{35}$S, chemiluminescent labels, fluorescent labels such as fluorescene or rodamine, and enzymatic labels such as horseradish peroxidase or alkaline phosphatase.

The hybridizing conditions used in the present invention include an annealing temperature of about 45–60° C., an extension temperature of about 70–75° C., and a denaturation temperature of about 90–95° C. for a total of about 30–50 cycles in a PCR mix containing a sufficient amount of buffer to maintain the pH at 8–8.5, and a sufficient amount of each of the following reagents to maintain: a final concentration of 50–200 μM of each dNTP; a final concentration of 0.1–2 μM primer; a final volume % of 5–15% glycerol; a final isopsoralen concentration of 25–150 μg/ml; and about 0.1–1 Units of AmpliTaq per 50 μl of the total volume of the reaction mixture.

TABLE 1*

Oligonucleotides for PCR detection of B. burgdorferi

| Target Gene | Oligonucleotide (base numbers) | Function | Nucleotide sequence, 5' to 3' |
|---|---|---|---|
| OSPA | OSPA149 (149-173) | Primer | TTA TGA AAA AAT ATT TAT TGG GAA T (SEQ ID NO:1) |
|  | OSPA319 (343-319) | Primer | CTT TAA GCT CAA GCT TGT CTA CTG T (SEQ ID NO:2) |
|  | OSPA459 (479-459) | Primer | ACT AAT GTT TTG CCA TCT TCT (SEQ ID NO:3) |
|  | OSPA6 (165-190) | Probe | ATT GGG AAT AGG TCT AAT ATT AGC CT (SEQ ID NO:4) |
|  | OSPA6' (196-216) | Probe | GCA TGT AAG CAA AAT GTT AGC (SEQ ID NO:5) |
| OSPB | OSPB1110 (1110-1132) | Primer | AAA CGC TAA ACA AGA CCT TCC TG (SEQ ID NO:6) |

TABLE 1*-continued

Oligonucleotides for PCR detection of B. burgdorferi

| Target Gene | Oligonucleotide (base numbers) | Function | Nucleotide sequence, 5' to 3' |
|---|---|---|---|
| | OSPB1411 (1437-1411) | Primer | AGC TTT GAG AGT TTC CTC TGT TAT TGA (SEQ ID NO:7) |
| Flagellin | FLA107 (107-131) | Primer | TTA ATC GAG CTT CTG ATG ATG CTG C (SEQ ID NO:8) |
| | FLA335 (362-335) | Primer | ATT TCG TCT GTA AGT TGC TCT ATT TCA A (SEQ ID NO:9) |

*Sequences are shown from 5' to 3' ends

BRIEF DESCRIPTION OF THE DRAWINGS

FIG. 1. Alignment of published DNA sequences for OSPA gene for various strains of *B. burgdorferi* (SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32). For clarity sake, only the nucleotide sequences at variance with the consensus sequence are shown. Highly conserved regions (Region 1:135–227; Region 2:316–343; Region 3:457–493) are underlined. Primers (OSPA149:149–173; OSPA319:319–343; OSPA459:459–479) are overlined. Sequences were aligned using the Pileup utility made available by Genetics Computing Group, Madison, Wis. Strain B31 sequence numbering was used. Genbank Accession numbers are indicated in parentheses.

DETAILED DESCRIPTION OF THE INVENTION

A method is presented for detecting the presence of the Lyme-disease causative agent, particularly the spirochete *Borrelia burgdorferi*, in biological samples using the polymerase chain reaction (PCR). Samples (bacterial cultures, tick extracts, or clinical specimens) are carefully processed such that DNA is isolated free from nucleases and polymerase inhibitors. PCR primers OspA149, OspA319 and OspA459, hybridizing to the OspA gene located on the 54-Kb extracellular plasmid in *B. burgdorferi*, have been developed with reference to the consensus sequence of 14 different strains. These primers are highly sensitive and specific for *B. burgdorferi*. PCR primers OspB1110 and OspB1411, hybridizing to the OspB gene located on the same plasmid, were developed with reference to the OspB sequence of strain B31 and also exhibit high specificity and sensitivity for all tested strains of *B. burgdorferi*. Primers for the genomic sequences fla, encoding a flagellin protein (FLA107 and FLA337), and 16S rDNA (DD02 and DD04), were also used but showed lower sensitivity in clinical studies than the primers associated with the extracellular plasmid DNA.

PCR reactions incorporate the use of isopsoralen, which is highly effective in preventing the occurence of false positive results. The method shows high specificity and sensitivity in the detection of Lyme disease from dilute samples, particularly synovial fluid, and is shown to produce direct evidence of the spirochete in patients with advanced Lyme arthritis whose synovial fluid does culture for *B. burgdorferi*.

The following examples are offered to further illustrate the various specific and preferred embodiments and techniques. It should be understood, however, that many variations and modifications may be made while remaining within the spirit and scope of the present invention.

EXPERIMENTAL EXAMPLES

Example 1

Sample Preparation and DNA Isolation

The diverse characteristics and DNA content of clinical samples require the use of different preparation methods. Specimens may contain nucleases (especially whole blood, serum, and urine) or Taq poLymerase inhibitors (especially blood and urine), which disallow direct use of the specimen for PCR. It is imperative that all clinical samples avoid contact with all sources of Borrelia DNA during collection, aliquot handling, and storage, or false-positive samples may occur. Avoid work areas where cultures, antigen preparations, or amplified DNAs have been manipulated. Samples are best sealed at the patient's bedside and sent directly to the PCR laboratory, where aliquots for serologic testing can be made.

A. Bacterial culture of *B. burgdorferi*. Borrelia isolates were grown in 7 ml of a modified BSK medium such as BSK H, a medium specifically developed for culture of *Borrelia burgdorferi* and available from Sigma Chemical, St. Louis, Mo., in screw-cap tubes (13 by 100 mm) at 32° C. Cell pellets were harvested from 1 ml of BSK culture containing $1 \times 10^9$ to $5 \times 10^9$ organisms per ml. The pellet was resuspended in 50 μl of TE buffer (TE buffer: 10 mM Tris-HCl, pH 8.0, 1 mM ethylene diamine tetraacetic acid (EDTA), both from Sigma Chemical Company, St. Louis, Mo.), and boiled for 10 minutes in a temperature block. A 10-fold dilution series was prepared in TE buffer, and PCR was performed directly on 1- to 5-μl aliquots.

B. Ticks. Ixodes ticks were identified. Live ticks are suitable for all test methods. Desiccation until testing was prevented. Dead ticks were stored in 70% alcohol prior to testing. Desiccated specimens could also be used. Whole ticks were processed as described in D. H. Persing et al., *Science*, 249, 1420–1423 (1990) and D. H. Persing et al., *J. Clin. Micro.*, 28, 566–572 (1990), which are incorporated herein by reference. Briefly, ticks were removed from alcohol and air dried on filter paper disks for 5 minutes. Each whole tick was placed in a 1.5-ml microcentrifuge tube, covered with 20 μl of K buffer (K Buffer: 10 mM Tris, pH 8.3, 50 mM KCl, 1.75 mM $MgCl_2$, 0.01% bovine serum albumin (BSA, Fraction V), 0.45% Tween 20, 0.45% Nonidet P-40 (all from Sigma Chemical Company, St. Louis, Mo.)) and a small volume of BSA-coated glass beads (0.1-mm glass beads, BioSpec Products, Bartlesville, Okla.), and crushed with a disposable plastic pestle or pipette tip. The buffer becomes slightly turbid when the tick contents are released. Tubes were heated in a 95° C. heating block for 10 minutes, and then immediately chilled on ice. PCR was used to test 5 µl of supernatant. Additional buffer was be added to large specimens as necessary.

C. Urine. Sample sizes of 15 ml were used, preferably collected prior to antibiotic therapy. An equal volume of 95% ethanol was added prior to storage in some protocols. Solvent extraction was used to isolate the DNA as follows:

1. Urine (500 µl) was added to a 1.5-ml microcentrifuge tube and centrifuged at 16,000× g for 5 minutes. The supernatant was removed and discarded, and the pellet was stored if needed for later processing at −20° C.
2. The pellet was resuspended in 246.2 µl of TE, 5 µl of 1 M dithiothreitol (DTT, Sigma Chemical Company, St. Louis, Mo.), 20 µl of 0.25 M EDTA (pH 8), 25 µl of 10% sodium dodecyl sulfate (Amresco, Inc., Solon Ohio), and 3.8 µl of 20-mg/ml proteinase K (VWR Scientific, Philadelphia, Pa.) and incubated 1 hour at 37° C.
3. The digest (approximately 300 µl) was transferred to pediatric serum separator tubes (Becton Dickinson, Bedford, Mass.). This product greatly simplifies solvent extraction, allowing multiple extractions to be performed in the same tube. Alternatively, the clinical specimen may be extracted directly by adding the specimen to the tube without digestion.
4. The sample was extracted with 150 µl of phenol-chloroform-isoamyl alcohol (25:24:1) (Amresco, Solon Ohio). Mixing was accomplished by inversion or vortexing, then the mixture was centrifuged at 16,000× g for 30 seconds. The aqueous layer is above the inert plug and the organic solvent layer. A second extraction was performed in the same tube.
5. Next the sample was extracted with 150 µl of chloroform-isoamyl alcohol (24:1) in the same tube.
6. The upper aqueous layer containing nucleic acids was transferred to a 1.5-ml microcentrifuge tube, and 30 µl of 3 M sodium acetate and 300 µl of isopropanol were added. The tube was gently inverted to mix.
7. The sample was centrifuged at 16,000× g for 15 minutes at 4° C. The supernatant was carefully removed by using a fine-tip pipette without disturbing the pellet.
8. The pellet was washed with 500 µl of 70% ethanol, then centrifuged at 16,000× g for 15 minutes at 4° C. All but 20 µl of ethanol was removed. The sample was evaporated to dryness in a Speed Vac centrifuge for 5 minutes. Air drying of the pellet is an alternative method.
9. The pellet was resuspended in 50 µl of TE and stored overnight at 4° C. to resolubilize the nucleic acid. Aliquots of 2.5 µl were used in a 100-µl PCR reaction.

D. Other body fluids.

1. Sample preparation.

Cerebrospinal fluid. Samples of 2 ml or more were used in sterile tubes. Aliquots were stored at −20° C. until use. Multiple freeze-thaw cycles were avoided.

Joint fluid. Samples of 2 ml or more were collected in a red-top tube (no anticoagulant) or a purple-top tube (ethylene diamine tetraacetic acid (EDTA) additive). Heparin tubes (green-top) were not used, since they inhibit PCR (Venoject tubes, available from Terumo Medial, Elkton, Md.). Aliquots were stored at −20° C. until use. Multiple freeze-thaw cycles were avoided.

Whole blood. Samples of 5 to 10 ml were collected in a purple-top tube (EDTA additive) and stored at 4° C. They were processed or aliquoted and frozen as soon as possible after receipt.

Serum. Samples of 1 to 3 ml were stored in a sterile tube at −20° C. until use. Multiple freeze-thaw cycles were avoided.

2. DNA isolation via chaotropic lysis/solvent extraction.

The IsoQuick Nucleic Acid Extraction Kit (MicroProbe Corp., Bothell, Wash.) employs chaotropic lysis to disrupt cells and stabilize the nucleic acid contained in a variety of clinical samples, including bacteria and whole blood (MicroProbe Corp., *IsoQuick Nucleic Acid Extraction Kit, Technical Insert*, MicroProbe Corp., Concord, Calif. (1991)). This kit was used to successfully isolate DNA from 100- to 200-µl volumes of joint fluid, CSF, plasma, serum, urine, and whole blood. The kit uses a modified solvent extraction method, which, in brief, includes guanidinium isothiocyanate lysis, partitioning of nucleic acid into an aqueous phase, and isopropanol precipitation of nucleic acid. The resulting nucleic acid was dissolved in 20 to 30 µl of RNase-free water (sterile water for irrigation USP, Baxter Healthcare), and 5 µl was used for PCR. Addition of 20 µg of glycogen (Boehringer Mannheim Biochemicals, Indianapolis, Ind.) per sample during alcohol precipitation improved the recovery of small quantities of nucleic acid.

E. Tissue. A single standard 3- to 5-mm skin punch biopsy or equivalent-sized tissue specimen was stored in 70% ethanol at room temperature. Tissue (i.e., skin biopsy specimen, BB-sized to pea-sized tissue biopsy specimen) was immersed in 50 to 100 µl of K buffer-proteinase K (K Buffer-proteinase K: K Buffer as described above in B. with 100 mg of proteinase K per ml (International Biotechnologies, Inc., New Haven, Conn.)) and incubated at 55° C. in a temperature block until digestion was complete. The amount and type of tissue determine the required incubation time, which typically ranges from 1 to 24 hours. Briefly vortexing the sample several times during incubation speeds tissue digestion. Samples were heated at 95° C. for 10 minutes to inactivate proteinase K and immediately chilled on ice. Excessive heating will decrease the DNA yield. Aliquots of 1 to 5 µl of digest were tested by PCR. Processed samples were stored at −20° C.

Example 2

PCR Amplification

1. DNA primers were synthesized on an oligonucleotide synthesizer (Applied Biosystems, Foster City, Calif.), desalted on an oligonucleotide-purification cartridge (Glen Research, Sterling, Va.), and used without further purification. Alternatively, they were purchased directly from Integrated DNA Technologies, Coralville, Iowa.

2. A PCR master mix was prepared with final concentrations of: 10 mM Tris HCl (pH 8.3), 50 mM KCl, 1.75 mM $MgCl_2$, 0.01% BSA, 200 µM of each deoxynucleoside triphosphate A, C, G, and T (dNTP) (Promega, Madison, Wis., or Boehringer Mannheim Biochemicals, Indianapolis, Ind.), 50 pmol of each primer per 50-ml reaction (1.0 mM), 10% glycerol, 100 µg/ml of isopsoralen compound 10 (HRI Associates, Inc., Concord, Calif.), 0.025 U/µl of AmpliTaq polymerase (Perkin-Elmer Cetus, Norwalk, Conn.). The following substitutions were necessary: for OSPA149/OSPA319, substitute 2.5 mM $MgCl_2$ for the 1.75 mM $MgCl_2$; for DD02/DD06, substitute 62.5 µM of each dNTP for the 200 mM of each dNTP, 50 µg/ml of isopsoralen compound 10 instead of 100 µg/ml, and 0.05 U/µl of AmpliTaq polymerase instead of 0.025 U/µl. In later experiments Ampliwax beads (Perkin-Elmer Cetus, Norwalk, Conn.) were added to prevent nonspecific hybridization at low temperatures. Isopsoralen was added to the reaction mixture for the second round but not the first round of the hemi-nested procedure for OSPA149/OSPA319, as described below. Processed DNA (5 µl) and 1 or 2 drops of mineral oil was added to 20 µl of the reaction mixture. All pipetting operations were performed with positive-displacement pipettors. It is useful to overestimate the volume of required master mix by one or two reactions to allow for pipetting inaccuracies and other volume losses during setup.

3. DNA was amplified in a thermal cycler by using a three-step protocol for the OSPA149/OSP319 target: denaturation at 94° C. for 45 seconds, annealing at 55° C. for 45 seconds, and extension at 72° C. for 45 seconds for a total of 50 cycles. A similar procedure was used for the OSPB1110/OSPB1411 target and the FLA107/FLA335 target: denaturation at 94° C. for 45 seconds, annealing at 50° C. for 45 seconds, and extension at 72° C. for 45 seconds for a total of 50 cycles. For these two targets the thermal cycling was preceded by a 4 minutes incubation at 94° C. and followed by a 7 minute extension at 72° C. For the DD02/DD06 target a two-step protocol was used: denaturation at 94° C. for 25 seconds and annealing at 60° C. for 25 seconds for a total of 50 cycles, and then heated to 72° C. for a 5-minute final extension. For the OSPA149/OSPA459 target a hemi-nested procedure was used: the first round of amplification utilized the primer pair OSPA149/OSPA459 and consisted of initial heating at 94° C. for 4 minutes, followed by 25 cycles of denaturation at 94° C. for 45 seconds, annealing at 50° C. and extension at 72° C., then a final 7 minute extension at 72° C. Upon completion, the following solution (75 µl) was added to the reaction mixture: 10 mM Tris HCl (pH 8.3), 50 mM KCl, 1.75 mM MgCl$_2$, 0.01% BSA, 200 mM of each dNTP A, C, G, and T, 50 pmol of each primer OSPA149 and OSPA319, 10% glycerol, isopsoralen compound 10 (100 µg/ml, HRI Associates, Inc., Concord, Calif.), 2.5 units of AmpliTaq polymerase (Perkin-Elmer Cetus, Norwalk, Conn.). The same cycling procedure was performed a second time.

4. The reaction tubes were removed from the DNA cycler and exposed to 20 mW/cm$^2$ of 300- to 400-nm UV light for 15 minutes at 4° C. in an HRI-100 UV Photochemical Reaction Chamber for post-PCR sterilization of amplicon (HRI Associates, Inc., Concord, Calif.). Postamplification inactivation of amplified DNA is optional; however, routine use significantly reduces the risk of laboratory contamination with amplified DNA.

5. A 4% agarose gel (3% NuSieve and 1% SeaPlaque or 1% SeaKem (FMC Bioproducts, Portland, Me.) agarose gel was prepared in 1× TBE buffer (20× TBE buffer: 216 g of Tris base (Sigma), 110 g of boric acid (Sigma), 80 ml of 0.5 M EDTA (pH 8.0; Sigma), H$_2$O to 1 liter). The PCR products were electrophoresed, 5 µl of product to 2 µl of gel-loading buffer (27 ml of glycerol, 3 ml of 10× TBE, 1 ml of 10% sodium dodecyl sulfate (SDS), 10 ml of 0.5 M EDTA (pH 8.0), 10 mg of bromphenol blue, H$_2$O to 100 ml) until the bromphenol blue indicator migrated at least two-thirds the length of the gel (35 to 100 V for 1 to 3 hours).

5. The amplification products were visualized after staining with ethidium bromide (Sigma Chemical Company, St. Louis, Mo.). Use of isopsoralen increased the apparent molecular weight of amplification products 10 to 25%.

6. The gel was denatured and neutralized by soaking in denaturation buffer (0.5 M NaOH, 1.5 M NaCl) for 45 minutes followed by neutralization buffer (0.5 M Tris (pH 7.5; Sigma), 1.5 M NaCl) for 15 minutes. The reaction products were then transferred to nylon membrane (Hybond N; Amersham Corp., Arlington Heights, Ill.) by Southern blot using 10× SSC transfer buffer (10× SSC: 1.5 M NaCl plus 0.15 M sodium citrate).

7. Positive amplification and sensitivity control was carried out as follows. DNA (60–100 pg) was prepared from a boiled *B. burgdorferi* B31 (ATCC 35210) bacterial culture. Use of both high-positive and low-positive reactions provided useful quality control information. DNA concentrations were determined as follows. A 10-fold dilution series of *B. burgdorferi* DNA was prepared, and 5-µl aliquots of each dilution were amplified. Two of the last DNA dilutions yielding positive amplification reactions were chosen for routine controls. The specificity controls were 1 ng each of *Borrelia hermsii* (ATCC 35209) and *Treponema pallidum* (ATCC 27087). The negative amplification control was prepared by adding 5 µl of water directly to the PCR master mix (triplicate).

Example 3

DNA Probe Hybridization and Detection of Amplification Products

1. Internal oligonucleotide probes (180 ng per hybridization) were synthesized on an oligonucleotide synthesizer (Applied Biosystems, Foster City, Calif.) and desalted on an oligonucleotide-purification cartridge (Glen Research, Sterling, Va.). Alternatively, they were purchased from Integrated DNA Technologies (Coralville, Iowa). The oligonucleotides were $^{32}$P-end-labeled. As an example, probe OspA6 was labeled by adding to a 1.5 µl microcentrifuge tube, the following: 12.3 µl water, 1.7 µl 10× T4 buffer, 1.0 µl probe, 1.0 µl T4 polynucleotide kinase, and 1.0 µl γ$^{32}$P ATP. This mixture was incubated for 45–60 minutes in a 37° C. water bath. The labeled probe was then heated at 95° C. for 6 minutes and cooled to room temperature to inactivate the kinase. In later experiments, amplification products were detected with a chemiluminescent internal hybridization probe constructed by amplification of internal sequences or by direct coupling of the amplification product itself with horseradish peroxidase as directed by the manufacturer for the ECL kit (Amersham Laboratories, Arlington Heights, Ill.). Briefly a 142 nucleotide probe was produced using primers OspA175 (GGT CTA ATA TTA GCC TTA ATA GC) (SEQ ID NO:10) and OspA316 (CAA TTA GAT CGT ACT TGC) (SEQ ID NO:11) and an annealing temperature of 46° C. with 72° C. for 72 minutes final extension. For full-length probes, the presence of PCR primer sequences in nonspecific amplification products did not result in lower hybridization specificity. For a detailed description of detection of PCR amplification products by means of a chemiluminescent probe, see D. H. Persing et al., *J. Clin. Microbiol.*, 30, 2097–2103 (1992), incorporated herein by reference.

2. Blots were prehybridized for 1 hour at 55° C. in 10 ml of hybridization solution (5× Denhardt's solution [1× Denhardt's solution is 0.02 percent Ficoll, 0.02 percent polyvinylpyrrolidone, and 0.02 percent BSA], 5× SSPE (Sigma Chemical Company 20× stock: 0.2 M phosphate, 2.98 M NaCl, 0.02 M EDTA), 0.5% SDS, 100 mg/mL of denatured salmon sperm DNA (Sigma Chemical, St. Louis, Mo.). Probe was added and hybridized for 3 hours at 55° C. All prehybridization, hybridization, and wash steps were performed in glass hybridization bottles and incubated in a hybridization oven (both from Hybaid Limited, Middlesex, UK).

3. The probe solution was decanted and the blots washed twice for 10 minutes with 150 ml of 2× SSC, 0.1% SDS; a third high-stringency wash was performed for 30 minutes at 55° C. with 150 ml of prewarmed 1× SSC, 0.1% SDS. Increased stringency may be achieved by repeating wash 3 or by adding a 15-minute wash with 150 ml of hybridization wash 2 containing 2% sodium pyrophosphate.

4. This Saran-wrapped blot was exposed to Kodak X-Omat film or Kodak XAR-5 film in an exposure cassette for up to 48 hours at −70° C. as necessary for adequate visualization.

Example 4

Multiple Target Detection of B. Burgdorferi-Specific Plasmid and Genomic Targets in Synovial Fluid Specimens Using DNA Primer Pairs OspA149/OspA319, OspB1110/OspB1411, DD02/DD06 and Fla107/Fla335

DNA primer pairs OspA149/OspA319 (Table 1), OspB1110/OspB1411 (Table 1), DD02/DD06 (DD02 sequence: CCC TCA CTA AAC ATA CCT (SEQ ID NO:12); DD06 sequence: ATC TGT TAC CAG CAT GTA AT) (SEQ ID NO:13) and Fla107/Fla335 (Table 1) were synthesized as described in Example 2. PCR experiments were conducted as described in Examples 2 and 3 on synovial fluid DNA from nineteen patients with chronic Lyme disease. The samples were aliquoted soon after collection in a biosafety hood kept free of contaminating B. burgdorferi DNA and then frozen at −70° C. or −20° C. until further analysis. The patients met Centers for Disease Control and Prevention case definition criteria for Lyme disease as set out in the Morbidity and Mortality Weekly Report. All patients had intermittent episodes of arthritis, lived in areas endemic for Lyme disease, and had elevated antibody titers for B. burgdorferi by ELISA (enzyme-linked immunosorbant assay). Eleven control synovial fluid specimens were collected from patients with non-Lyme arthritic disorders and were processed and sorted the same way as those from patients with Lyme arthritis.

As shown in Table 2, all 19 synovial fluid specimens from the Lyme arthritis patients reacted with the extracellular OspA149/OspA319 primer pair and the extracellular OspB1110/OspB1411 primer pair, while only 8 or the 19 samples of the same volume reacted with the genomic 16S rDNA primer pair (DD02/DD06) and only 9 of 17 samples were positive for the flagellin target (FLA107/FLA35).

TABLE 2

Polymerase chain reaction detection of B. burgdorferi-specific plasmid and genomic targets in synovial fluid specimens

| | Plasmid Targets | | Genomic Targets | | Culture result |
|---|---|---|---|---|---|
| Specimen No. | OspA | OspB | 16S rDNA | Flagellin | |
| 1 | + | +/+ | − | − | − |
| 2* | + | +/+ | − | − | − |
| 3 | + | +/+ | − | − | − |
| 4 | +/+ | +/+ | − | +(weak) | − |
| 5 | + | +/+ | − | − | − |

TABLE 2-continued

Polymerase chain reaction detection of B. burgdorferi-specific plasmid and genomic targets in synovial fluid specimens

| | Plasmid Targets | | Genomic Targets | | Culture result |
|---|---|---|---|---|---|
| Specimen No. | OspA | OspB | 16S rDNA | Flagellin | |
| 6 | +/+ | +/+ | + | + | −†‡ |
| 7 | + | +/+ | − | QNS | − |
| 8 | +/+ | +/+ | + | − | − |
| 9 | + | +/+ | − | − | −† |
| 10 | +/+ | +/+ | + | + | −† |
| 11 | +/+ | +/+ | +/+ | +/+ | −† |
| 12 | +/+ | +/+ | + | +/+ | − |
| 13 | + | +/+ | − | − | − |
| 14 | +/+ | +/+ | + | + | −† |
| 15 | + | +/+ | | − | − |
| 16 | +/+ | +/+ | − | +/+ | − |
| 17 | +/+ | +/+ | + | + | − |
| 18 | +/+ | +/+ | − | + | − |
| 19 | +/+ | ND | + | ND | − |
| 20–30 (negative controls) | − | | − | − | ND |

ND, not done; +, positive on blot only; +/+, positive on ethidium bromide-stained gel and blot.
*Specimens 2 and 3 were from same patient.
†Culture done on fresh specimen (all others done on previously frozen specimens).
‡Culture positive from erythema migrans lesion 1 year earlier; azithromycin treatment failed.

Example 5

Detection of B. Burgdorferi-Specific Plasmid and Genomic Targets in Synovial Fluid Specimens Using DNA Primer Pairs OspA149/OspA319, OspA2/OspA4 and DD02/DD06

Synovial fluid was collected from Lyme arthritis patients treated in the Lyme disease clinics at Yale-New Haven Hospital (1975–1987) or New England Medical Center (1987–1992) over a 17-year period. Synovial fluid was also collected from control patients with other forms of arthritis during the same period. Primer pairs OspA149/OspA319, OspA2/OspA4 and DD02/DD06, and related oligonucleotide probes as described in Table 3 were synthesized and end-labeled as described in Examples 2 and 3. Samples were processed, PCR reactions conducted, and amplification products detected as described in Examples 2 and 3.

TABLE 3

Oligonucleotide Primer and Probe Sequences

| OLIGONUCLEOTIDES (BASE NO.) | SEQUENCE* |
|---|---|
| Set 1 | |
| Primers | |
| OspA2 (943-920) | GTT TTG TAA TTT CAA CTG CTG ACC (SEQ ID NO:14) |
| OspA4 (788-812) | CTG CAG CTT GGA ATT CAG GCA CTT C (SEQ ID NO:15) |
| Probe | |
| OspA3 (906-881) | GCC ATT TGA GTC GTA TTG TTG TAC TG (SEQ ID NO:16) |
| Set 2 | |
| Primers | |
| OspA319 (343-319) | CTT TAA GCT CAA GCT TGT CTA CTG T (SEQ ID NO:2) |
| OspA149 (149-173) | TTA TGA AAA AAT ATT TAT GGG AAT (SEQ ID NO:1) |
| Probe | |
| OspA6' (196-216) | GCA TGT AAG CAA AAT GTT AGC (SEQ ID NO:5) |
| Set 3 | |
| Primers | |
| OspA319 (343-319) | CTT TAA GCT CAA GCT TGT CTA CTG T (SEQ ID NO:2) |
| OspA149 (149-173) | TTA TGA AAA AAT ATT TAT GGG AAT (SEQ ID NO:1) |
| Probe | |
| OspA6 (165-190) | ATT GGG AAT AGG TCT AAT ATT AGC CT (SEQ ID NO:5) |
| Set 4 | |
| Primers | |
| DD02 (1472-1455) | CCC TCA CTA AAC ATA CCT (SEQ ID NO:12) |
| DD06 (1105-1124) | ATC TGT TAC CAG CAT GTA AT (SEQ ID NO:13) |
| Probe | |
| BR01 (1304-1350) | GAT TGA AGT CTG AAA CTC GAC TTC ATG AAG TTG GAA TCG CTA GTA AT (SEQ ID NO:17) |

*Sequences are shown from 5' to 3'.

As shown in Table 4 below, *B. burgdorferi* DNA was detected with at least one of the primer-probe sets in 75 out of the 88 patients with Lyme arthritis. The three OspA primer sets, which probe for extrachromosomal DNA, each detected *B. burgdorferi* DNA in 75 to 89% of the 75 patients with positive test results. Primer set 4, which detected genomic DNA, was less sensitive; only 56 percent of the 75 patients had positive results with this set. No *B. burgdorferi* DNA was found in any of the 69 control patients or in the blank control samples. Importantly, *B. bergdorferi* DNA was detected in 70 of 73 (96%) Lyme-disease patients who had not received antibiotic treatment or were tested prior to treatment.

TABLE 4

PCR Results in Synovial Fluid from Case and Control Patients

| | Primer-Probe Sets | | | | |
|---|---|---|---|---|---|
| | SET 1 | SET 2 | SET 3 | SET 4 | ANY SET |
| | | | no. of patients | | |
| Lyme arthritis (n = 88) | | | | | |
| Positive PCR results | 57 | 56 | 67 | 42 | 75 |
| Negative PCR results | 31 | 32 | 21 | 46 | 13 |

TABLE 4-continued

PCR Results in Synovial Fluid from Case and Control Patients

| | Primer-Probe Sets | | | | |
|---|---|---|---|---|---|
| | SET 1 | SET 2 | SET 3 | SET 4 | ANY SET |
| | | | no. of patients | | |
| Other arthritis (n = 64) | | | | | |
| Positive PCR results | 0 | 0 | 0 | 0 | 0 |
| Negative PCR results | 12 | 12 | 57 | 57 | 64 |

Example 6

Sequence Alignment and Identification of Highly Conserved Regions and Primer Pairs for OspA Gene Sequences for the gene OspA from fourteen strains of *B. burgdorferi* were aligned with the Pileup utility of the GCG Sequence Analysis Package (Genetics Computing Group, Madison, Wis.). See FIG. 1. The numbering system used in FIG. 1 is that of the B31 strain, strictly for ease of reference. Included in the alignment set were two newly identified isolates, Dn127 and 25015 (GenBank accession number S88693) that exhibited sequences that differed substantially from the previously known sequences. Comparison of the aligned sequences permitted generation of a consensus sequence (a textual string of nucleotides representing the most commonly found base at each site on the gene) and identification of the most highly conserved regions among all the strains. These regions, labeled Region 1 (135 through and including 227), Region 2 (316 through and including 371) and Region 3 (457 through and including 493) were utilized as the basis for oligonucleotide primer generation. The program OLIGO (OLIGO Primer Analysis Sorgware version 4.0 for the Macintosh, National Biosciences, Inc. Plymouth, Minn.) was used to generate preliminary compatible primer sets, which upon visual inspection suggested primers OspA149 (nucleotides 149–173), OspA319 (nucleotides 319–343) and OspA459 (nucleotides 459–479) as likely candidates for successful PCR reactions, based upon their melting points, interaction energies and predicted secondary structure. These primers were synthesized and tested as described in Examples 2 and 3.

The foregoing detailed descriptions and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of detecting in a biological sample the presence of Lyme-disease causing spirochetes comprising:

(a) amplifying DNA isolated from the biological sample with a primer pair that targets portions of extrachromosomal linear plasmid gene encoding outer surface protein A of the Lyme-disease causing spirochetes; wherein a first primer of said primer pair hybridizes to the complement of Borrelia burgdorferi consensus sequence having SEQ ID NO:32 and a second primer of said primer pair hybridizes to the Borrelia burgdorferi consensus sequence having SEQ ID NO:32, wherein the first primer of said primer pair comprises nucleotides 135–227 of SEQ ID NO:32 or a portion thereof, and wherein the second primer of said primer pair comprises the complement of nucleotides 316–371 of SEQ ID NO:32 or a portion thereof or comprises the complement of nucleotides 457–493 of SEQ ID NO:3 or a portion thereof, and wherein the primers do not hybridize to Borrelia hermsii DNA or Treponema pallidum DNA;

(b) probing said amplified DNA with a labeled gene probe so as to form a complex comprising said amplified DNA and labeled gene probe; and (c) detecting the presence or absence of the complex, wherein the presence of the complex is indicative of the presence of Lyme-disease causing spirochetes in the biological sample.

2. A method of detecting in a biological sample the presence of Lyme-disease causing spirochetes comprising:

(a) amplifying DNA isolated from the biological sample with a primer pair that targets portions of extrachromosomal linear plasmid gene encoding outer surface protein A of the Lyme-disease causing spirochetes; wherein one primer of said primer pair hybridizes to the complement of nucleotides 135–227 of the Borrelia burgdorferi consensus sequence having SEQ ID NO:32, and wherein the other of said primer pair hybridizes to nucleotides 316–371 or nucleotides 457–493 of the Borrelia burgdorferi consensus sequence having SEQ ID NO:32, wherein the primers do not hybridize to *Borrelia hermsii* DNA or *Treponema pallidum* DNA;

(b) probing said amplified DNA with a labeled gene probe so as to form a complex comprising said amplified DNA and labeled gene probe; and (c) detecting the presence or absence of the complex, wherein the presence of the complex is indicative of the presence of Lyme-disease causing spirochetes in the biological sample.

3. The method of claim 1 or 2 wherein the Lyme-disease causing spirochetes are of the genus Borrelia.

4. The method of claim 3 wherein the Lyme-disease causing spirochetes are *Borrelia burgdorferi* spirochetes.

5. The method of claim 1 or 2 wherein the biological sample is a fluid or tissue sample from a human patient.

6. The method of claim 5 wherein the biological sample is synovial fluid.

7. The method of claim 1 or 2 wherein the step of amplifying the isolated DNA comprises using a polymerase chain reaction mix containing an amount of isopsoralen effective to inactivate the amplified product.

8. The method of claim 1 wherein one primer is primer OspA149 (SEQ ID NO:1).

9. The method of claim 1 wherein one primer is primer OspA319 (SEQ ID NO:2).

10. (Third amendment) The method of claim 1 wherein one primer is primer OspA459 (SEQ ID NO:3).

11. The method of claim 1 wherein the primer pair consists of primers OspA149 (SEQ ID NO:1) and OspA319 (SEQ ID NO:2).

12. The method of claim 1 wherein the primer pair consisting of primers OspA149 (SEQ ID NO: 1) and OspA459 (SEQ ID NO:3).

13. The method of claim 1 or 2 wherein portions of the labeled probe consist of sequences comprising the *Borrelia burgdorferi* consensus sequence having SEQ ID NO:32 or a portion thereof.

* * * * *

UNITED STATES PATENT AND TRADEMARK OFFICE
CERTIFICATE OF CORRECTION

PATENT NO.: 6,087,097
DATED: Jul. 11, 2000
INVENTOR(S): Persing

It is certified that errors appear in the above-identified patent and that said Patent is hereby corrected as shown below:

In column 13, Table 3 (Second column of table);

For oligonucleotide names OspA6, delete: "(SEQ ID NO:5)" and insert --(SEQ ID NO:4)--, therefor.

Signed and Sealed this

Seventeenth Day of April, 2001

*Attest:*

NICHOLAS P. GODICI

*Attesting Officer*   Acting Director of the United States Patent and Trademark Office